US006828094B2

(12) United States Patent
Kilger et al.

(10) Patent No.: US 6,828,094 B2
(45) Date of Patent: Dec. 7, 2004

(54) METHOD FOR THE UNCOUPLED, DIRECT, EXPONENTIAL AMPLIFICATION AND SEQUENCING OF DNA MOLECULES WITH THE ADDITION OF A SECOND THERMOSTABLE DNA POLYMERASE AND ITS APPLICATION

(75) Inventors: Christian Kilger, Heidelberg (DE); Svante Pääbo, Leipzig (DE); Michael Motz, Heidelberg (DE)

(73) Assignee: Roche Diagnostics GmbH, Mannheim (DE)

(*) Notice: Subject to any disclaimer, the term of this patent is extended or adjusted under 35 U.S.C. 154(b) by 0 days.

(21) Appl. No.: 09/339,103

(22) Filed: Jun. 24, 1999

(65) Prior Publication Data
US 2002/0034792 A1 Mar. 21, 2002

Related U.S. Application Data

(63) Continuation-in-part of application No. 08/991,184, filed on Dec. 16, 1997, now Pat. No. 6,225,092.

(30) Foreign Application Priority Data

Dec. 20, 1996 (DE) ......................................... 196 53 494

(51) Int. Cl.$^7$ ............................ C12Q 1/68; C12P 19/34
(52) U.S. Cl. .......................... 435/6; 435/91.1; 435/91.2
(58) Field of Search ........................ 435/6, 91.1, 91.2, 435/810

(56) References Cited

U.S. PATENT DOCUMENTS

| | | | | |
|---|---|---|---|---|
| 4,962,020 A | | 10/1990 | Tabor et al. ................... | 435/6 |
| 5,310,652 A | * | 5/1994 | Gelfand et al. ................ | 435/6 |
| 5,409,811 A | | 4/1995 | Tabor et al. .................... | 435/6 |
| 5,427,911 A | | 6/1995 | Ruano ........................... | 435/6 |
| 5,432,065 A | | 7/1995 | Fuller ........................ | 435/91.1 |
| 5,512,462 A | | 4/1996 | Cheng ....................... | 435/91.2 |
| 5,525,492 A | * | 6/1996 | Hill .......................... | 435/91.2 |
| 5,556,772 A | | 9/1996 | Sorge et al. ............... | 435/91.2 |
| 5,614,365 A | | 3/1997 | Tabor et al. ................... | 435/6 |
| 5,677,152 A | * | 10/1997 | Birch et al. ................ | 435/91.2 |
| 5,773,258 A | * | 6/1998 | Birch et al. ................ | 435/91.2 |
| 5,789,168 A | | 8/1998 | Leushner et al. .............. | 435/6 |
| 5,830,657 A | | 11/1998 | Leushner et al. .............. | 435/6 |
| 5,928,906 A | * | 7/1999 | Koster et al. .............. | 435/91.2 |

FOREIGN PATENT DOCUMENTS

| | | |
|---|---|---|
| EP | 0 727 496 | 8/1996 |
| EP | 0 771 870 | 5/1997 |

OTHER PUBLICATIONS

Chemical Abstracts, vol. 125, No. 25, 1996, p. 393, 125:319052.
Deng et al., Journal of Microbilogical Methods, vol. 17 (1993) 103–113, "Simultaneous amplification and sequencing of genomic DNA (SAS) . . . ".
Hwang et al., Analytical Biochemistry, vol. 231, No. 2, Nov. 1995, pp. 460–463, "Direct automated sequencing of singl lambda–phage plaques by exponential amplification sequencing".
International Publication No. WO 97/42348, published Nov. 13, 1997.
International Publication No. WO 97/41257, published Nov. 6, 1997.
International Publication No. WO 97/41258, published Nov. 6, 1997.
International Publication No. WO 97/41259, published Nov. 6, 1997.
International Publication No. WO 97/40939, published Nov. 6, 1997.
International Publication No. WO 97/23650, published Jul. 3, 1997.
International Publication No. WO 96/41014 published Dec. 19, 1996.
International Publication No. WO 96/10640 published Apr. 11, 1996.
International Publication No. WO 94/26766 published Nov. 24, 1994.
International Publication No. WO 93/02212, published Feb. 4, 1993.
Kilger et al., Biol. Chem., vol. 378, pp 99–105, Feb. 1997, "Direct exponential Amplification and Sequencing (DEXAS) of Genomic DNA".
Kilger et al., Nucleic Acids Research, vol. 25, No. 10, May 1997, pp. 2032–2034"Direct DNA sequence determination from total genomic DNA".
Rao, Analytical Biochemistry, vol. 216, 1–14 (1994), "Direct–Sequencing of Polymerase Chain Reaction–Amplified DNA".
Sarkar et al., Nucleic Acids Research, 1995, vol. 23, No. 7, pp 1269–1270, "Semi Exponential cycle sequencing".
Tabor et al., Proc. Natl. Acad. Sci. USA, vol. 92, pp 6339–6343, Jul. 1995, "A single residue in DNA polymerases of the *Escherichia coli* DNA polymerase 1 family is critical for distinguishing between deoxy–and dideoxyribonucleotides".

\* cited by examiner

*Primary Examiner*—Kenneth R. Horlick
(74) *Attorney, Agent, or Firm*—Arent Fox PLLC

(57) ABSTRACT

Method for sequencing a nucleic acid molecule in a thermocycling reaction which initially comprises a nucleic acid molecule, a first primer, a second primer, a reaction buffer, a first thermostable DNA polymerase, (optionally) a thermostable pyrophosphatase, deoxynucleotides or derivatives thereof and a dideoxynucleotide or a derivative thereof and which is characterized in that the thermocycling reaction additionally contains a second thermostable DNA polymerase which, in comparison to the said first thermostable DNA polymerase, has a reduced ability to incorporate dideoxynucleotides as well as the use of the said method.

138 Claims, 8 Drawing Sheets

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "oligonucleotide"

(xi) SEQUENCE DESCRIPTION: SEQ ID NO: 1:

GGCTGGTCCT GCCGCTGCTT GTCAT                                           25

(2) INFORMATION FOR SEQ ID NO: 2:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "oligonucleotide"

(xi) SEQUENCE DESCRIPTION: SEQ ID NO: 2:

CTGCTCCCCA GTGGATCGGG TGTAAAC                                         27

(2) INFORMATION FOR SEQ ID NO: 3:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: other nucleic acid
      (A) DESCRIPTION:   /desc = "oligonucleotide"

(xi) SEQUENCE DESCRIPTION: SEQ ID NO: 3:

CACCTTTGGG GTGGTGACAA GTGTGAT                                         27

(2) INFORMATION FOR SEQ ID NO: 4:

(i) SEQUENCE CHARACTERISTICS:
      (A) LENGTH: 24 base pairs
      (B) TYPE: nucleic acid

```
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 4:

CGACGTTGTA AAACGACGGC CAGT                                          24

(2) INFORMATION FOR SEQ ID NO: 5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "oligonucleotide"

(xi) SEQUENCE DESCRIPTION: SEQ ID NO: 5:

CAGGAAACAG CTATGAC                                                  17
```

METHOD FOR THE UNCOUPLED, DIRECT, EXPONENTIAL AMPLIFICATION AND SEQUENCING OF DNA MOLECULES WITH THE ADDITION OF A SECOND THERMOSTABLE DNA POLYMERASE AND ITS APPLICATION

This is a continuation-in-part application of U.S. patent application Ser. No. 08/991,184, filed on Dec. 16, 1997, U.S. Pat. No. 6,225,092, the disclosure of which is incorporated by reference herein.

FIELD OF THE INVENTION

The present invention relates to a method for the uncoupled, direct, exponential amplification and sequencing of DNA molecules by the addition of a second thermostable DNA polymerase and it also relates to the application of the said method. The uncoupled, direct, exponential amplification and sequencing of DNA molecules by the addition of a second thermostable DNA polymerase is referred to as "DEXTAQ" in the following.

DESCRIPTION OF THE RELATED ART

The DNA sequence determination as developed by Sanger et al. ((1977) Proc. Natl. Acad. Sci. USA 74, 5463–5467) is usually carried out with a T7 DNA polymerase (Tabor S. and Richardson, C. C. (1989) Proc. Natl. Acad. Sci. USA 86, 4076–4080). This method requires relatively large amounts of a purified, single-stranded DNA template. Recently cycle sequencing has been developed (Murray, V. (1989) Nucleic Acids Res. 17, 8889). This method does not require a single-stranded template and allows the sequence reaction to be initiated with relatively small amounts of template. However, the template DNA has to be purified to almost complete homogeneity and is usually prepared by means of cloning in plasmids (Bolivar, F. et al., (1977) Gene 2, 95–113) and subsequent plasmid purification (Birnboim, H. C. and Doly, J. (1979) Nucleic Acids Res. 7, 1513–1523) or by means of PCR amplification (Mullis, K. B. and Faloona, F. A. (1987) Methods Enzymol. 155, 335–350). Only one primer is used in both of the methods described above.

In one embodiment of the cycle sequencing which is referred to as "coupled amplification and sequencing" or "CAS" Ruano and Kidd ((1991) Proc. Natl. Acad. Sci. USA 88, 2815–2819; U.S. Pat. No. 5,427,911) have shown that one can use a two-step protocol to generate sequences from DNA templates. In the first step 15 PCR cycles are carried out with Taq DNA polymerase in the absence of dideoxynucleotides in order to prepare an adequate amount of sequencing template. In a second step in which dideoxynucleotides and a labelled primer are added, CAS produces the sequence as well as the additional amplification of the target sequence. Two primers are used in both steps of the method.

Many DNA polymerases, including the Taq DNA polymerase, that are used in coupled DNA sequencing reactions strongly discriminate against ddNTPs and preferably incorporate dNTPs if they are furnished with a mixture of ddNTPs as well as dNTPs. Hence the optimization of the CAS process requires careful titration of the dideoxynucleotides.

Furthermore since coupled amplification and sequencing depends on the amount of the initial DNA, the distance between the two primers and the concentrations and the ratios of the ddNTPs and dNTPs relative to one another, the optimization of coupled amplification and sequencing reactions (CAS) requires that the reaction conditions are individually optimized for a particular DNA fragment.

Other known thermostable polymerases that are used for sequencing, e.g. ThermoSequenase and Taquenase, carry a mutation which is known as the "Tabor Richardson" mutation (Tabor, S. & Richardson, C. C. (1995) Proc. Natl. Acad. Sci. USA 92, 6339–6343) in which a tyrosine is present instead of a phenylalanine in the cleft of the enzyme which, during polymerization of the DNA molecule being formed, is responsible for discriminating between the incorporation of either deoxynucleotides or dideoxynucleotides. Such enzymes or functional derivatives thereof have an increased ability to incorporate dideoxynucleotides into DNA fragments that are being formed and can be used to improve the signal uniformity in sequencing reactions. The increased ability of the aforementioned DNA polymerases with a Tabor-Richardson mutation to incorporate dideoxynucleotides increases the statistical probability that a chain termination occurs due to incorporation of a dideoxynucleotide into a DNA molecule being formed.

Therefore according to the present state of the art it would be expected that the use of a thermostable polymerase which carries a Tabor-Richardson mutation would limit the distance at which the two primers could be placed on the DNA molecule to be sequenced. This in turn restricts the choice of primers that can be used in a given sequencing reaction.

All the methods described above require an interruption between the first step for the exponential amplification of the template DNA and the second step for the synthesis of truncated DNA molecules and they also require the individual optimization of a given DNA fragment which can be tedious and time-consuming and can lead to errors especially when sequencing a large number of different DNA molecules or when processing large amounts of samples in a hospital or laboratory or when sequencing rare samples for forensic or archaeological studies.

For this reason it would be advantageous to have available a method for sequencing nucleic acids which simultaneously potentiates the exponential amplification of molecules of complete length and of molecules of shortened length in the reaction which leads to a reduction of the required amount of starting nucleic acid molecules and does not require an interruption of the exponential amplification step and of the sequencing step so that the whole reaction can be carried out more rapidly and with fewer manipulations.

Furthermore it would also be advantageous to have available a method for sequencing nucleic acid molecules which allows an increase in the distance between the positions of the two primers on the nucleic acid molecule to be sequenced, is relatively independent of the distance between the said primers and in general does not require an optimization of the reaction conditions for each DNA fragment to be sequenced.

SUMMARY OF THE INVENTION

An object of the present invention is to provide an improved, rapid and reliable method for sequencing nucleic acid molecules.

A further object of the present invention is to provide a method for sequencing nucleic acid molecules that can be carried out in an uninterrupted manner, in a single step and in a single container.

A further object of the present invention is to provide a nucleic acid sequencing method which simultaneously increases the exponential amplification of molecules of complete length as well as of molecules of shortened length which leads to a reduction of the initial amount of nucleic acid molecules that are required for the cycling reaction.

A further object of the present invention is to provide a method for sequencing nucleic acid molecules which leads to an increase in the distance at which both primers can be positioned on the nucleic acid molecule to be sequenced.

A further object of the present invention is to provide a method for sequencing a nucleic acid which increases the signal-to-noise ratio of specific, correctly terminated molecules to unspecifically terminated molecules.

A further object of the present invention is to provide an application of the method according to the invention for sequence determination in medical diagnostics, forensics and population genetics.

Further objects of the invention can be deduced by a person skilled in the art from the description.

The thermocycling reaction of the present invention comprises a first primer and a second primer which serve to simultaneously produce sufficient template molecules of complete length as well as molecules of shortened length which contribute to the sequencing of the nucleic acid molecule. Either one primer is labelled and the other is not or both are differently labelled. In addition each reaction initially contains the nucleic acid template to be sequenced as well as a buffer solution and the four deoxynucleotides or derivatives thereof and one dideoxynucleotide or another terminating nucleotide e.g. 3'-aminonucleotides or 3'-ester-derivatized nucleotides. A thermostable pyrophosphatase can be optionally added. Four reaction mixtures are prepared one for the determination of each base.

However, in contrast to the methods known in the state of the art, it was surprisingly found that direct, exponential amplification and sequencing can be carried out by adding two different types of DNA polymerases to the initial cycle sequencing reaction: a first thermostable DNA polymerase and a second thermostable DNA polymerase with a reduced ability to incorporate dideoxynucleotides compared to the said first thermostable DNA polymerase. The first DNA polymerase mainly produces shortened products that accumulate exponentially during the cycles and contribute to the sequence ladder that is generated whereas the second DNA polymerase, which has a reduced ability to incorporate dideoxynucleotides compared to the first said thermostable DNA polymerase, primarily produces products of complete length which accumulate exponentially and serve in subsequent cycles as a template for the production of further DNA strands of complete length as well as templates for extensions which contribute to the sequencing reaction. Hence the combination of the different properties of the two polymerases, i.e. the ability of the first DNA polymerase to efficiently incorporate dideoxynucleotides and the ability of the second DNA polymerase to efficiently incorporate deoxynucleotides, leads to a considerably increased efficiency of the uncoupled, direct, exponential amplification and sequencing reaction.

Therefore the present invention provides a method for nucleic acid sequencing (DEXTAQ) which simultaneously enables the exponential amplification of molecules of complete length as well as of short length in a thermocycling reaction and leads to a reduction of the amount of initial nucleic acid molecules that are necessary for the reaction. This enables the sequencing of single-copy DNA fragments in amounts as small as ca. 60 ng genomic DNA.

Since, in addition, all reagents that are necessary for the exponential amplification of fragments of complete length as well as of shortened fragments are present in the initial reaction mixture, the method of the present invention (DEXTAQ) achieves the simultaneous, exponential production of a sequencing template and of a sequence ladder in a single tube without the necessity of interrupting the thermocycling reaction. This means that using the method of the present invention it is possible to determine the nucleic acid sequence in a single step.

Furthermore the method of the present invention (DEXTAQ) allows the distance at which the two primers can be positioned on the template nucleic acid molecule to be enlarged. Thus the method according to the invention for example enables the 3'-ends of the first and of the second primer to be positioned on the DNA template at a distance that is larger than or equal to 500 bases.

Hence the aforementioned object of the present invention is achieved by providing a method for sequencing nucleic acid molecules in a thermocycling reaction which initially contains a nucleic acid molecule, a first primer, a second primer, a reaction buffer, a first thermostable DNA polymerase, deoxynucleotides or derivatives thereof, and a dideoxynucleotide or another terminating nucleotide and is characterized in that the thermocycling reaction additionally contains a second thermostable DNA polymerase which, in comparison to the said first thermostable DNA polymerase, has a reduced ability to incorporate dideoxynucleotides.

A single enzyme would also be suitable for use in the method according to the invention that has different enzyme activities e.g. by using a chimeric polymerase or by the fact that a fraction of the polymerase has a modified ability to incorporate dideoxynucleotides by the continuous or partial action of agents. If this enzyme is composed of several subunits then these subunits can be covalently or non-covalently linked together.

The present invention also enables three or more DNA polymerases to be used in this method.

In a preferred embodiment the method according to the invention is furthermore characterized in that each thermocycling reaction for the determination of the position of A, G, C and T in the said DNA molecule is carried out in a single step, in a single container, vessel or tube.

The use of a DNA polymerase is preferred as the thermostable first DNA polymerase which, in contrast to wild-type Taq DNA polymerase, has a reduced discrimination against ddNTPs in the buffer and under the conditions that are used for the thermocycling. More preferably a DNA polymerase is used which carries a "Tabor-Richardson" mutation or a functional derivative thereof which also has no 5'-3'exonuclease activity such as e.g. AmplitaqFS (Taq DNA polymerase (-exo5'-3') (F667Y), Tabor and Richardson (1995), loc. cit.), Taquenase (Taq DNA polymerase 235 (-exo5'-3') (F667Y), Tabor and Richardson (1995), loc. cit.) and ThermoSequenase (Taq DNA polymerase 272 (-exo5'-3') (F667Y), Tabor and Richardson (1995), loc. cit.) as well as mixtures thereof or other DNA polymerases and mixtures thereof which are thermostable can also be used in the method of the present invention. The use of Thermosequenase or some other DNA polymerase which has a better ability to incorporate ddNTPs is particularly preferred for the method of the present invention.

A DNA polymerase which carries no "Tabor-Richardson" mutation such as e.g. Taq DNA polymerase, Tth DNA polymerase, Klentaq (Taq DNA polymerase) (-exo5'-3'), (Korolev et al. (1995) Proc. Natl. Acad. Sci. USA 92, 9246–9268, W. Barnes in Proc. Natl., Acad. Sci. USA 91 (1994), 2216–2220 and U.S. Pat. No. 5,436,149 is preferably used as the thermostable second DNA polymerase which has a reduced ability to incorporate dideoxynucleotides compared to the first thermostable DNA polymerase. The use of Taq DNA polymerase in the method of the present invention is particularly preferred.

Processive polymerases are preferably used for the method according to the invention i.e. the polymerase with a reduced discrimination against ddNTPs preferably has a higher processivity than ThermoSequenase and the polymerase which discriminates against ddNTPs preferably has a higher processivity than the wild-type Taq DNA polymerase. Polymerases according to the invention are most preferably used for the present method whose processivity is higher than that of the wild-type Taq DNA polymerase. Hence it would for example be advantageous to use two polymerases whose processivity is the same as that of T7 polymerases with thioredoxin.

The method according to the invention can also be carried out as a "hot start" method. In the "hot start" method, the polymerase or polymerases are inhibited at lower temperatures and the activity of the polymerase or polymerases only starts at an increased temperature in order to suppress polymerization on unspecifically hybridized primers at lower temperatures. One possibility is that the thermocycling reaction additionally contains a polymerase-inhibiting agent. Polymerase antibodies are, for example, commercially available which inhibit a polymerase and only denature at higher temperatures thereby releasing enzyme activity at higher temperatures. However, polymerases modified by genetic engineering that are present in an inactive form at lower temperatures would also be conceivable.

A preferred embodiment of the present invention is a method for the uncoupled, direct, exponential amplification sequencing of DNA molecules with a first, time released, hot-start thermostable DNA polymerase and a second thermostable DNA polymerase that discriminates against ddNTPs and its application. In variation of this embodiment, a second hot-start thermostable DNA polymerase that discriminates against ddNTPs is used. Another preferred embodiment is the above method whereas both the first and second thermostable DNA polymerases are time-released and hot-start enzymes, respectively.

The thermocycling reaction of the preferred embodiment of the present invention comprises a first primer and a second primer which serve to produce sufficient template molecules of complete length as well as molecules of shortened length which contribute to the sequencing of the nucleic acid molecule. Either one primer is labelled and the other is not or both are differently labelled. In addition, each reaction initially contains the nucleic acid template to be sequenced as well as a buffer solution and the four deoxynucleotides or derivatives thereof and at least one dideoxynucleotide or another terminating nucleotide e.g. 3'-aminonucleotides or 3'-ester-derivatized nucleotides. A thermostable pyrophosphatase can be optionally added. Four reaction mixtures are prepared one for the determination of each base.

In the preferred "hot start" embodiment, the reaction may also contain an antibody that is able to inhibit one or more of the polymerases present in the reaction. Optionally instead of using an antibody, the polymerase can be inhibited by another polymerase-inhibiting agent (see e.g. EP 0771 870 A1, the disclosure of which is incorporated by reference).

An embodiment of this hot-start sequencing method using a time released polymerase is described in more detail in the following:

It was found that direct, exponential amplification and sequencing can be carried out by adding two different types of DNA polymerases to the initial cycling reaction: a first thermostable DNA polymerase and a second thermostable DNA polymerase, which has a reduced ability to incorporate dideoxynucleotides compared to the first thermostable DNA polymerase. In this embodiment of the hot-start sequencing method, the first DNA polymerase, which mainly produces shortened products that accumulate exponentially during the cycles and contribute to the sequencing ladder that is generated, is inhibited by a polymerase-inhibiting agent and has to be released thereof to regain its polymerization activity. The polymerization-inhibiting agent reversibly loses inhibitory activity at a defined temperature and at a defined time point during the cycle sequencing reaction. Until the first DNA polymerase is released from its inhibitory agent, the second DNA polymerase, having a reduced ability to incorporate dideoxynucleotides compared to the first thermostable DNA polymerase, produces products of complete length which accumulate exponentially and serve in subsequent cycles as templates for the production of further DNA strands of complete length, as well as templates for extensions, which contribute to the sequencing reaction. The sequencing reaction will start after the polymerase-inhibiting agent is released from the first DNA polymerase. The combination of the two different properties of the two polymerases, i.e. the ability of the first DNA polymerase ("1") to efficiently incorporate dideoxynucleotides and the ability of the second DNA polymerase ("2") to efficiently incorporate deoxynucleotides, together with the separation of the amplification and sequencing processes by the polymerase-inhibiting agent from the beginning of the cycle sequencing reaction up to a defined number of cycles at which the polymerase-inhibiting agent looses its ability to inhibit, leads to a considerably increased efficiency of the uncoupled, direct, exponential amplification and sequencing reaction. Both the full length product and the sequencing ladder signals show marked increases in signal strength. Therefore, the sequential hot-start DEXTAQ method provides a method for nucleic acid sequencing which can take into account the amount of starting DNA by defining how many cycles of mere amplification are performed before the sequencing reaction starts (see FIG. 6).

FIG. 6 shows two experiments, (A) one in which a small amount of DNA is used as a substrate and (B) one in which more substrate DNA is present. Initially, the first DNA polymerase is inhibited by a polymerase-inhibiting agent, while the second DNA polymerase is allowed to be active thereby amplifying the substrate DNA in what constituting an amplification phase. By releasing the polymerase-inhibiting agent for the first DNA polymerase only after the amplification phase, this amplification phase can be performed for any given cycle number without the influence of another polymerase. Thus, more thermal cycles can be performed when starting from little DNA (A) or fewer thermal cycles can be performed when starting from more DNA (B).

Another especially preferred embodiment of this invention is the use of an antibody against a polymerase and an polymerase-inhibiting agent. For instance, the second polymerase, which discriminates against ddNTP's, is inhibited by an antibody against the second polymerase, whereas the first polymerase is inhibited by another polymerase-inhibiting agent. Examples of another polymerase-inhibiting agent are dicarboxylic acid anhydrides, such as citraconic anhydride, cis-aconitic anhydride, phthalic anhydride, maleic anhydride and succinic anhydride, or dianhydrides, such as pyromellitic dianhydride and naphthalenetetracarboxylic dianhydride. This would result in a release of the second polymerase at higher temperatures in early cycles of the reaction whereas the first polymerase is released only in later cycles of the reaction. In an especially preferred embodiment of this invention, agents are added to the reaction mixture which lower the melting point of the DNA, such agents can be, for example, glycerine, trehalose and other such agents as betaine or DMSO known to a person skilled in the art.

This methodology which includes a controlled release of various enzymes from inhibition and thereby adding their activities sequentially or simultaneously to an ongoing reaction without opening the tube or vessel can be applied to numerous combinations of enzymes. A further example is the simultaneous amplification and sequencing of RNA. Here, the reverse transcriptase carrying enzyme may be active from the start, whereas additional enzymes for amplification sequencing remain inactive until released. Thus, reverse transcription may occur without potentially inhibiting effect of other enzymes. One may also envision the combination of an amplification enzyme and a DNA modifying enzyme. Here, the first could amplify the target which is subsequently modified after the release of the second enzyme.

Polymerases which can be used for the sequential hot-start method are described in the following: The use of a DNA polymerase (DNA polymerase "1") is preferred as the thermostable first DNA polymerase which, in contrast to wild type Taq DNA polymerase, has a reduced discrimination against ddNTPs in the buffer and under the conditions that are used for the thermocycling and is inhibited by a polymerase-inhibiting agent (e.g. a polymerase-inhibting agent disclosed in EP 0 771 870 A1, the disclosure of which is incorporated by reference). The polymerase-inhibiting agent loses inhibitory activity by incubating the reaction mixture at an elevated temperature as part of the amplification reaction or during the sequencing reaction. More preferably a DNA polymerase is used which carries a "Tabor-Richardson" mutation or a functional derivative thereof which also has no 5'-3'exonuclease activity such as e.g. Amplitaq FS™ (Taq DNA polymerase (-exo5'-3') (F667), Tabor, S. & Richardson, C. C. (1995) Proc. Natl. Acad. Sci. USA 92, 6339–6343, Taquenase™ (Taq DNA polymerase (272 (-exo5'-3') (F667), Tabor and Richardson (1995),loc. cit.) as well as mixtures thereof or other DNA polymerases and mixtures thereof which are thermostable can also be used in the method of the present invention. The use of Thermosequenase or some other DNA polymerase which has a better ability to incorporate ddNTPs is particularly preferred for the method of the present invention.

Sequential hot-start sequencing ladders are shown in FIG. 7. Both processes, amplification and sequencing, are performing with high efficiency and therefore earlier production of a sequencing ladder can be observed and the accuracy is improved.

To produce the data shown in FIG. 7, 200 ng human genomic DNA was subjected to an uncoupled direct exponential amplification and sequencing reaction using 6 pmol of each IRD 700 and IRD 800 labelled Primer (mtDNA1: 5'-GATTCTAATTTAAACTATTCTCTGTTC-3'; mtDNA2: 5'-TTATGACCCTGAAGTAGGAACCAGATG-3'). The primers span a region of 521 base pairs of the human mitochondrial control region. The reactions were carried out using 2.5 U Taq DNA polymerase, 0.5 U of Pyrophosphatase and 9 U Amplitaq FS (FIG. 2A) and 9 U Ampli Taq FS Gold (FIG. 2B). The gel picture in FIG. 7A was obtained when the reaction was stopped at different cycles: 2, 4, 6, 8, 10, 12, 16, 20, 25, 30, 35 with the sequencing reaction performed as follows: 95° C. for 7 min then 35 cycles of 95° C. for 40 s, 62° C. for 20 s, and 70° C. for 60 s. The A.L.F to process 378 bases with 11 ambiguities for the IRD 700 labelled primer. The gel picture in FIG. 7B was obtained when the reaction was stopped at different cycles: 2, 4, 6, 8, 10, 12, 15, 20, 25, 30, 35. The cycle sequencing reaction was performed as follows: 15 cycles of 95° C. for 20 s, 62° C. for 20 s, 68° C. for 60 s, then 95° C. for 7 min, then 20 cycles of 95° C. for 40 s, 62s. At a condition of 95° C. for 7 min., there was the releasing step of the DNA polymerase "1" (EP 0 771 870), which carries the Tabor Richardson mutation for efficient incorporation of dideoxynucleotides. The A.L.F. software was able to process 400 bases with 2 ambiguities for the IRD 700 labelled primer.

In a further preferred embodiment of the method of the invention the ratio of the said primers is preferably higher than 1:1, more preferably between about 2:1 and about 3:1 and most preferably 2:1.

In a further preferred embodiment of the method of the invention the said primers have a length that can prevent annealing to unspecific DNA fragments by a high temperature during the cycling. This leads to a good signal-to-noise ratio. The said primers preferably have a length of at least 18 nucleotides.

Primers can be synthesized by means of methods known in the state of the art. For example primers can be synthesized using known methods which do not significantly change the stability or function of the said primers during the nucleic acid sequencing method of the present invention.

Furthermore PNA-DNA hybrid oligonucleotides (see Finn, P. J. et al., N.A.R. 24, 3357–3363 (1996), Koch, T. et al., Tetrahedron Letters, 36, 6933–6936 (1995), Stetsenko, D. A, et al., Tetrahedron Letters 37, 3571–3574 (1996), Bergmann, F. et al., Tetrahedron Letters 36, 6823–6826 (1995) and Will, D. W. et al., Tetrahedron 51, 12069–12082 (1995)) are also regarded as primers for the method according to the invention.

In a further preferred embodiment of the method of the invention the said first primer is labelled. Moreover it is preferable that the said first primer and second primer are labelled differently. Any agents or methods known in the state of the art can be used as single or differential labelling agents and methods, provided that the stability or function of the said primer in the DNA sequencing method of the present invention is not significantly changed. For example single and differential labels can be selected from the group which comprises those enzymes such as -galactosidase, alkaline phosphatase, peroxidase and enzyme substrates, coenzymes, dyes, chromophores, fluorescent, chemiluminescent and bioluminescent labels such as FITC, Cy5, Cy5.5, Cy7, Texas-red and IRD40 (Chen et al., (1993), J. Chromatog. A 652: 355–360 and Kambara et al. (1992), Electrophoresis 13: 542–546) ligands or haptens such as e.g. biotin and radioactive isotopes such as $^3H$, $^{35}S$, $^{32}P$, $^{125}I$ and $^{14}C$.

DEXTAQ is relatively insensitive to various buffers and various deoxynucleotides and dideoxynucleotide concentrations.

The number of thermocycles can be from about 18 to about 50 cycles depending on the amount of template DNA and its purity.

Buffer components which can be used can include Tris-HCl at a pH of about 9.0 to 9.5 and at a concentration of about 10 to 30 mM, ammonium sulfate at a concentration of about 10 to 20 mM, preferably 15 mM, MgCl$_2$ at a concentration of about 3.5 to 5.5 mM, optionally about 0.05 mM mercaptoethanol, about 0.28% Tween 20 and/or about 0.02% Nonidet 40. Buffer components, however, are not limited to these.

Deoxynucleotides may be selected from, but not limited to, dGTP, dATP, dTTP and dCTP. However, according to the invention, it is also possible to use derivatives of deoxynucleotides. Deoxynucleotide derivatives are defined as those deoxynucleotides or modified deoxynucleotides which are able to be incorporated by a thermostable DNA polymerase into growing DNA molecules that are synthesized in a thermocycling reaction. Examples of deoxynucleotide derivatives include thionucleotides, 7-deaza-2'-dGTP, 7-deaza-2'-dATP, as well as deoxyinosine triphosphate, that can also be used as a substitute deoxynucleotide for dATP, dGTP, dTTP or dCTP. However, deoxynucleotide derivatives are not limited to these examples. The aforementioned deoxynucleotides and derivatives thereof are preferably used at a concentration of about 300 µM to about 2 mM.

Dideoxynucleotides include, but are not limited to, ddGTP, ddATP, ddTTP and ddCTP. According to the invention, it is also possible to use derivatives of dideoxynucleotides which are defined as those dideoxynucleotides that are able to be incorporated by a thermostable DNA polymerase into growing DNA molecules that are synthesized in a thermo-cycling reaction. Preferred concentrations of ddNTPs are between about 1 µM and about 5 µM.

The preferred ratio of dNTPs to ddNTPs (dNTPs:ddNTPs) that is used in the method according to the invention is between about 100:1 and about 1000:1 more preferably between about 300:1 and about 600:1.

In a further preferred embodiment of the method of the invention the said method is carried out at a temperature at which the signal-to-noise ratio of the specific, shortened DNA molecules compared to the unspecific DNA molecules is large enough not to substantially impede reading of the sequence. In the case of human single-copy DNA sequences the highst possible annealing temperature drastically reduces the background. For this the annealing and synthesis steps of the thermocycling reaction are carried out at a temperature of at least about 55° C., preferably at about 66° C. and most preferably at at least about 68° C.

In a further preferred embodiment of the method of the invention, the nucleic acid molecule to be sequenced can be present as total genomic DNA which is in an uncloned or unpurified state. The genomic DNA can have a length of more than or equal to 2 kb. DEXTAQ functions with about 60 ng total genomic DNA, but also functions with smaller amounts of DNA if multicopy fragments are analysed. Other forms of DNA that can be used as templates include purified, partially purified or unpurified cloned DNA such as e.g. unpurified plasmid DNA from bacterial colonies or cloned or uncloned mitochondrial DNA etc. Furthermore the method of the present invention is relatively independent of the base composition of the template.

In a further preferred embodiment of the method of the invention the nucleic acid molecule to be sequenced can be present as RNA. A mixture of two polymerases is used: a first DNA polymerase according to the invention e.g. one which contains a "Tabor-Richardson" mutation or a functional derivative thereof, such as ThermoSequenase and a second DNA polymerase that is able to reversely transcribe RNA into DNA and has the ability to act as a PCR enzyme. Any thermostable DNA polymerase which has reverse transcriptase activity can be used as a second DNA polymerase for the method of the invention in which RNA is used as the template. Taq DNA polymerase (Jones et al., Nucl. Acids Res. 17:8387–8388 (1989)) or Tth DNA polymerase (Myers et al., Biochemistry 30:7666–7672 (1991)) is preferably used and more preferably Tth DNA polymerase. Tth polymerase reversely transcribes the RNA template into DNA which can then be used by both enzymes: Tth polymerase will primarily generate products of complete length which can serve as templates and ThermoSequenase will produce shortened products (ddNTP incorporation) and thus a sequence ladder.

Suitable buffers include those that are described in Myers et al. (1991) Biochemistry 30: 7666–7672. The following buffer can be used for both polymerases and guarantees the function of both polymerases: 10 mM Tris-HCl (pH 8.3), 40 mM KCl, 1 mM MnCl$_2$. A reverse transcription using a reaction buffer and optionally MgCl$_2$ at a concentration of about 1 mM to 5 mM and which also includes both polymerases, both primers and nucleotides, is subjected to an incubation step (15 minutes at 70° C.). Afterwards the MgCl$_2$ concentration is adjusted to between 1 mM and 5 mM and a DEXTAQ reaction is carried out.

In a preferred embodiment of the invention, a DNA polymerase from Carboxydothermus hydrogenoformans is used to sequence RNA. This enzyme disclosed in EP 0 834 569 has reverse transcriptase activity in the presence of Mg ions without the presence of Mn ions. In one of the embodiments of the invention, the polymerase is mutated as described in Tabor and Richardson (Tabor, S. & Richardson, C. C. (1995) Proc. Natl. Acad. Sci. USA 92, 6339–6343; EP 0 655 506) in order to create an enzyme that does not discriminate against ddNTPs. In this set-up Mg is present from the beginning in a range between 0.5 mM and 20 mM, no extra Mn is required. A suitable buffer additionally may comprise but is not limited to Tris-HCl (pH 6.5 to 11), KCl (2 mM-100 mM), ammoniumsulphate (2 mM-100 mM) and additional enzymes, such as thermostable pyrophosphatase (0,1–50 U). In addition, at least one nucleotide must be present. The reactions are cycled as disclosed above. The enzyme thus can contain activities to perform the reactions of reverse transcription, amplification and sequencing.

The present invention provides for the first time a method which enables the simultaneous amplification and sequencing of a nucleic acid fragment to be sequenced from a Complex Mixture of nucleic acids, such as total genomic human DNA, without prior amplification of the nucleic acid to be sequenced by means of known methods, in a single step i.e. without interrupting the reaction and indeed such that an unequivocal sequence ladder is readable.

The method of the invention can be used for the direct sequencing of nucleic acid molecules in a Complex Mixture. Complex Mixtures are nucleic acid mixtures in which no enriching purification for the target nucleic acid molecule has been performed. However, the nucleic acid may have been isolated from its original source, e.g. cells. In Complex Mixtures, the ratio of the total number of nucleotides in the target nucleic acid molecule and in the background nucleic acid molecules is substantially smaller than one and the ratio of the number of the target nucleic acid molecule to the number of the background nucleic acid molecules is not greatly larger than one, or even smaller than one, and possibly even substantially smaller than one. For instance, the ratio of the number of the target nucleic acid molecule to the number of the background nucleic acid molecules can range from about 0.0001 to about 1. Such Complex Mixtures can be a whole human genomic DNA containing a single copy of a human gene (e.g. CCR-5 gene) as the target DNA molecule for direct sequencing by the method of the invention. Table 1c shows an example of the Complex Mixture.

The method according to the invention can also be used for the direct sequencing of nucleic acid molecules in a Medium Complex Mixture. Medium Complex Mixtures are nucleic acid mixtures in which no enriching purification for the target nucleic acid molecule has been preformed. However, the nucleic acid may or may not have been isolated from its original source, e.g. bacterial cells. In Medium Complex Mixtures, the ratio of the total numbers of nucleotides in the target nucleic acid molecule and in the background nucleic acid molecules is close to or smaller than one and the ratio of the number of the target nucleic acid molecule to the number of the background nucleic acid molecules is larger than one. For instance, the ratio of the number of the target nucleic acid molecule to the number of the background nucleic acid molecules can range from about 1 to about 1,000. Such Medium Complex Mixtures can be DNA from a bacterial colony (containing plasmid DNA as the target DNA molecule), DNA from phage plaques (containing M 13 DNA as the target DNA molecule), or partially purified or unpurified mitochondrial DNA. Table 1b shows an example of the Medium Complex Mixture.

The method according to the invention can also be used for the direct sequencing of template nucleic acid molecule in a Non-Complex Mixture. Non-Complex Mixtures are nucleic acid mixtures in which the template nucleic acid has been amplified and/or purified or partially purified. The amplification and purification methods can be cloning with subsequent plasmid purification, gradient centrifugation and purification, or the product of PCR in which the PCR product may or may not be purified (the number of PCR cycles in the absence of terminating nucleotides may range from 1 to 50). In Non-Complex Mixtures, the ratio of the number of the target nucleic acid molecule and the number of background nucleic acid molecules is much larger than one. For instance, the ratio of the number of the target nucleic acid molecule to the number of the background nucleic acid molecules can range from about 1,000 to about $1 \times 10^{18}$. Table 1a shows an example of the Non-Complex Mixture.

Suitable sources of nucleic acid molecules in the method according to the invention are body fluids such as sperm, urine, blood or fractions of these, hairs, an individual cell, cells or fractions thereof, hard tissue such as bones and soft tissue or fractions thereof and cell cultures or fractions thereof as well as bacteria, viruses or bacteriophages.

The present invention also provides an application of the method according to the invention for the determination of a nucleotide sequence of a given nucleic acid molecule e.g. for sequencing Shotgun gene libraries using two labels for large-scale genome projects and in medical diagnostics, forensics and population genetics. The method of the present invention can be used to detect genetic mutations or polymorphisms, to identify the origin of the sequenced nucleic acid or to detect the presence of foreign or infectious agents in a sample.

A particular advantage of the method according to the invention is therefore the ability to directly sequence nucleic acids. Thus the method according to the invention can be used for the direct sequencing of e.g. eukaryotic genomic DNA such as e.g. of human, chromosomal DNA or mitochondrial DNA, human RNA, unpurified plasmid DNA from bacterial colonies as well as unpurified single-stranded or double-stranded DNA from bacteriophages.

The present invention relates to all combinations of all procedures of the above methods.

After preparation the sequencing reactions can be applied directly to a sequencing gel such as e.g. after addition of a commonly used loading buffer (e.g. formamide which contains 20 mM EDTA (pH 7.4) and 6 mg/ml dextran blue) and denaturation (e.g. for 4 minutes at 96° C.). The sequence ladder can be read in correspondence with known methods. The method of the invention is well suited for automation. Since the two primers in the reaction are provided with different labels which can for example be detected with two different wavelengths, the method of the present invention enables the simultaneous sequencing of both strands of a template and the detection of both reactions in one or several gel lanes. In general many DEXTAQ reactions using different dyes can be carried out simultaneously in the same tube and applied to a sequencing instrment that is equipped with several lasers or can be detected by other methods such as e.g. autoradiography.

Furthermore a kit for sequencing a nucleic acid molecule is also a subject matter of the present invention, wherein this kit contains a reaction buffer, deoxynucleotides or derivatives thereof and at least one dideoxynucleotide or a derivative thereof and at least one thermostable DNA polymerase with different abilities to incorporate dideoxynucleotides. A suitable first primer and the second primer are then added individually depending on the application and the nucleic acid molecule to be sequenced.

In order to sequence a nucleic acid molecule the kit contains, in a preferred embodiment, a first thermostable DNA polymerase and additionally a second thermostable DNA polymerase which, compared to the said first thermostable DNA polymerase, has a reduced ability to incorporate dideoxynucleotides.

Most preferably the kit for sequencing a nucleic acid molecule contains a first thermostable polymerase, Taq DNA polymerase (-exo5'-3') (F667Y) or a functional derivative thereof and a second thermostable DNA polymerase, Taq polymerase or a functional derivative thereof.

Figure 1:
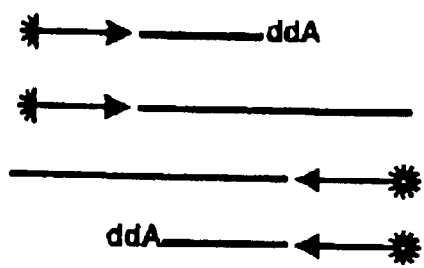
FIG. 1. Schematic representation of the method of the present invention (DEXTAQ). A first polymerase of the present invention (A) which carries a "Tabor-Richardson" mutation for discriminating towards ddNTPs preferentially incorporates ddNTPs and produces the sequence ladder. A second polymerase of the present invention which, compared to the said first thermostable DNA polymerase (B), has a reduced ability to incorporate dideoxynucleotides, preferably incorporates dNTPs and mainly produces products of complete length and provides the uncoupled, direct, exponential amplification and sequence reaction with additional sequencing templates.
Figure 1:
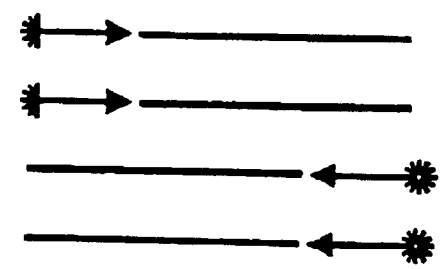

The invention is described more exactly and in more detail by the following non-limiting examples.

EXAMPLE 1

Template Preparation

Total genomic DNA was prepared from 2 ml blood samples using a rapid cleaning kit (Cambridge Molecular Technologies Ltd., Cambridge, UK). Purified DNA was diluted in ddH$_2$O to a concentration of 175 ng per µl.

Sequencing Reagents and Conditions

Unlabelled and FITC-labelled oligonucleotides were synthesized with an ABI DNA/RNA Synthesizer, Model 392. Cy5 labelled oligonucleotides were obtained from the Pharmacia Biotech Company (Freiburg, Germany). The following oligonucleotides were used:

SEQ ID NO. 1:
(CCR5-1): 5'-GGC TGG TCC TGC CGC TGC TTG TCA T-3';

SEQ ID NO. 2:
(CCR5-2): 5'-CTG CTC CCC AGT GGA TCG GGT GTA AAC-3';

SEQ ID NO. 3:
(CCR5-3)5'-CAC CTT TGG GGT GGT GAC AAG TGT GAT-3' (Samson, M. et al., Biochemistry 35 (11), 3362–3367 (1996)), SEQ ID NO. 4:
(universal primer) 5'-CGA CGT TGT AAA ACG ACG GCC AGT-3' and SEQ ID NO. 5:
(reverse) 5'-CAG GAA ACA GCT ATG AC-3' (Pharmacia Biotech).

Direct, exponential amplification and sequencing reactions were carried out using Thermosequenase reagents (2). A 24 µl mixture composed of 6 pmol of an FITC-labelled and 3 pmol of an unlabelled primer, 6 pmol of an FITC-labelled and 3 pmol of a Cy5-labelled primer, or 3 pmol of an FITC-labelled and 3 pmol of an unlabelled primer, total genomic DNA (0.5 to 8 µl at a concentration of 120 ng/µl) and additional polymerase if necessary (0.1 to 2_µl depending on the unit definition) was prepared and 6 µl aliquots were added to 2 µl Thermosequenase termination mix. The sequencing reactions were carried out in a thermocycler with a heatable cover (MJ-Research, Watertown, Mass.). The reactions were stopped by adding 5 µl formamide (20 mg EDTA (pH 7.4) and 6 mg/ml dextran blue) which was followed by a 4 minute denaturation at 95° C. The sequencing reactions were analysed on an A.L.F. (Pharmacia Biotech, Uppsala, Sweden). HydroLink Long Ranger (FMC, Rockland, Me.) gels and 30 cm glass plates were used in all cases. The gel conditions corresponded to the manufacturer's recommendations.

EXAMPLE 2

Two oligonucleotides with a length of 25 and 27 nucleotides which span 3 82 base pairs of the CCR5 gene were synthesized. One of the two oligonucleotides was labelled at the 5'-end with fluorescein (CCR5-2) whereas the other (CCR5-1) was unlabelled. Two reactions were prepared each containing 6 pmol of the labelled primer and 3 pmol of the unlabelled primer, 500 ng total genomic DNA and ThermoSequenase reagent which was composed of enzyme, reaction buffer and deoxy and dideoxy mixtures. 2.5 units of standard Taq polymerase was added to one of the two reactions. The reactions were incubated for 3 min. at 95° C. in order to enable a complete denaturation of the template DNA. Afterwards 45 cycles were carried out each consisting of 30 sec. at 68° C. and 40 sec. at 95° C. The reactions were stopped and denatured by the addition of formamide and heating to 95° C. for 4 minutes before they were applied to an A.L.F. sequencing apparatus.

If no additional Taq DNA polymerase had been added, the A.L.F. was able to process 344 bases. If, in contrast, 0.25 units Taq polymerase was added to the direct exponential amplification and sequencing reaction, 351 bases were determined. A visual analysis of the A.L.F. curves showed that the signal intensity improved where Taq DNA polymerase had been added. Furthermore the stops at the start of the run which can occur in direct exponential amplification and sequencing reactions were substantially reduced. In contrast the signal strength remained continuously high towards the amplifying primer. In contrast in the case in which no Taq DNA polymerase was present, the signal was weaker after 200 base pairs. The signal at the end of the run which corresponds to the product of complete length was substantially stronger in the reaction in which Taq DNA polymerase was present.

EXAMPLE 3

In order to confirm the fact that additional Taq DNA polymerase is able to amplify the exponential factor and to reduce the background and also to determine the amount of Taq DNA polymerase required for an optimal reaction, a reduced amount of template DNA was used in combination with varying amounts of Taq DNA polymerase. Five reactions were prepared each containing 120 ng total genomic DNA, 6 pmol of the labelled primer and 3 pmol of unlabelled primer and ThermoSequenase reagent. In one reaction no additional Taq DNA polymerase was added. In the other 4 reactions 0.25, 0.5, 1.0 and 2.0 units Taq polymerase was added respectively. In order to exclude a possible effect of the Taq polymerase storage buffer, the storage buffer was added to that reaction to which no polymerase had been added. The reactions were subjected to the cycles described above.

In the case where no Taq DNA polymerase had been added the A.L.F. Manager was only able to process a few bases and the signal intensities were too low to be considered useful for routine sequencing. In the reactions in which 0.25 units and 0.5 units had been added the A.L.F. Manager was able to process 374 bases and 364 bases respectively. 226 bases were determined by the A.L.F. Manager in the reaction in which one unit Taq polymerase had been added.

Figure 2:
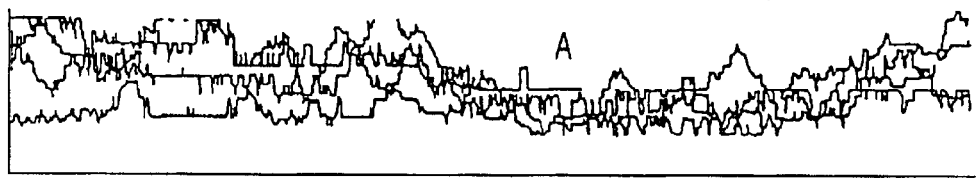
FIG. 2. 60 ng of total genomic DNA was subjected to a direct, uncoupled sequencing reaction using 6 pmol of an FITC-labelled primer (CCR5-2) and 3 pmol of an unlabelled primer (CCR5-1). The section shown in all windows is only at a distance of 20 base pairs from the end of the template and the last bases are part of the primer that generates the second template. No additional Taq DNA polymerase was added to the reaction that is shown in window A. Increasing amounts of Taq DNA polymerase were added to the reactions that are shown in window B (0.25 units), C (0.5 units), D (1.0 units) and E (2.0 units). In cases where no Taq DNA polymerase had been added, the A.L.F. software was not able to process a sequence. A better ratio between signal and noise is seen in the cases in which Taq DNA polymerase had been added.
Figure 2:
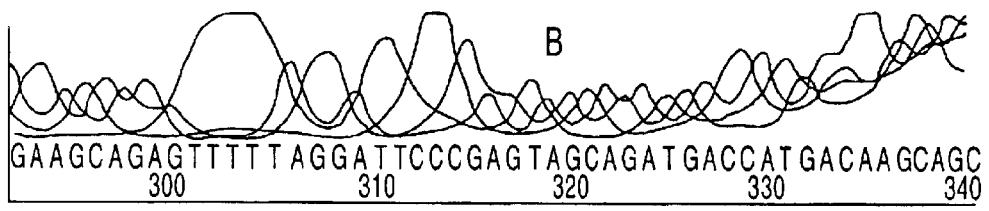
Figure 2:
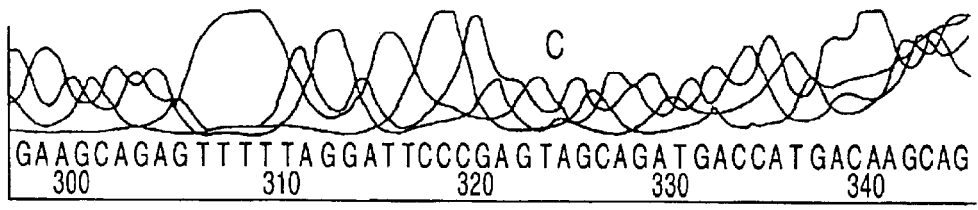
Figure 2:
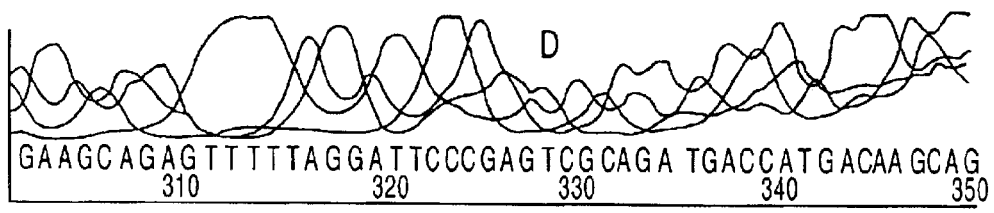
Figure 2:
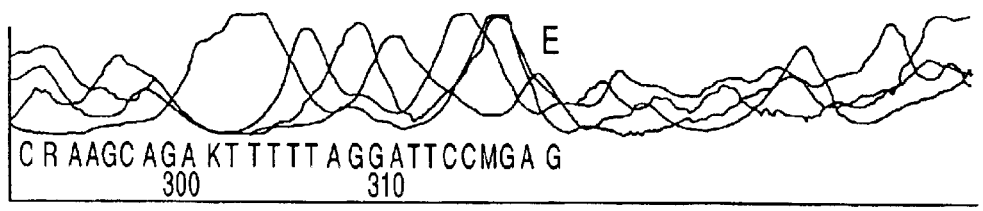
Figure 2A:
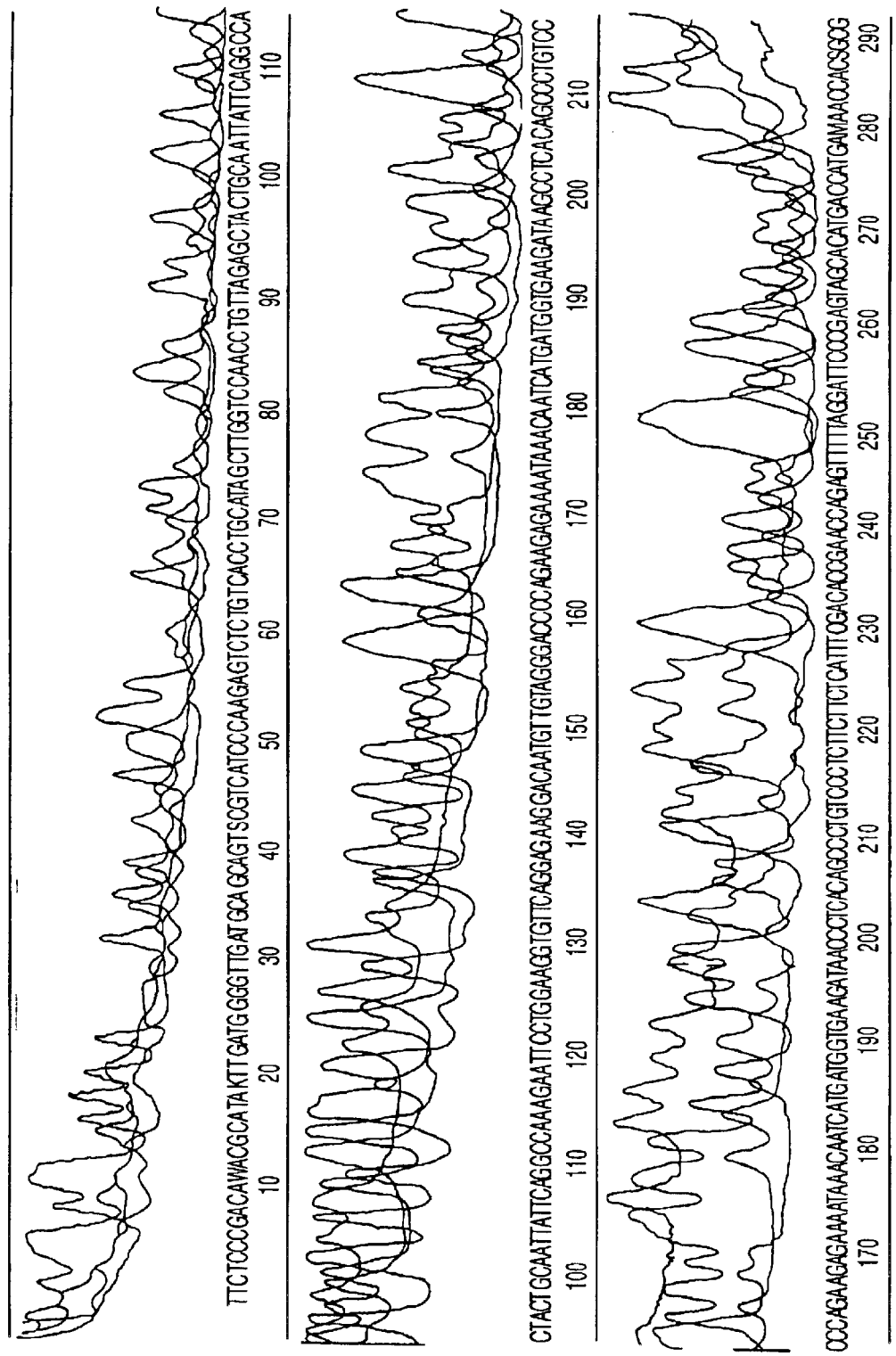
FIG. 2A. 60 ng of total genomic DNA was subjected to an uncoupled, direct amplification and sequencing reaction using equimolar amounts i.e. 3 pmol each of an FITC-labelled primer (CCR5-2) and of an unlabelled primer (CCR5-1). The A.L.F. software was able to process 290 bases. The reactions were carried out using 0.25 units Taq DNA polymerase and standard ThermoSequenase reagents.

The reactions were repeated under identical conditions but using an even smaller amount of genomic DNA. 60 ng template DNA was sequenced using varying amounts of Taq DNA polymerase. No signal was detectable where no Taq polymerase had been added but the A.L.F. Manager was again able to process the sequence in cases where between 0.1 and 0.4 units Taq DNA polymerase had been added (FIG. 2).

EXAMPLE 4

Figure 3:
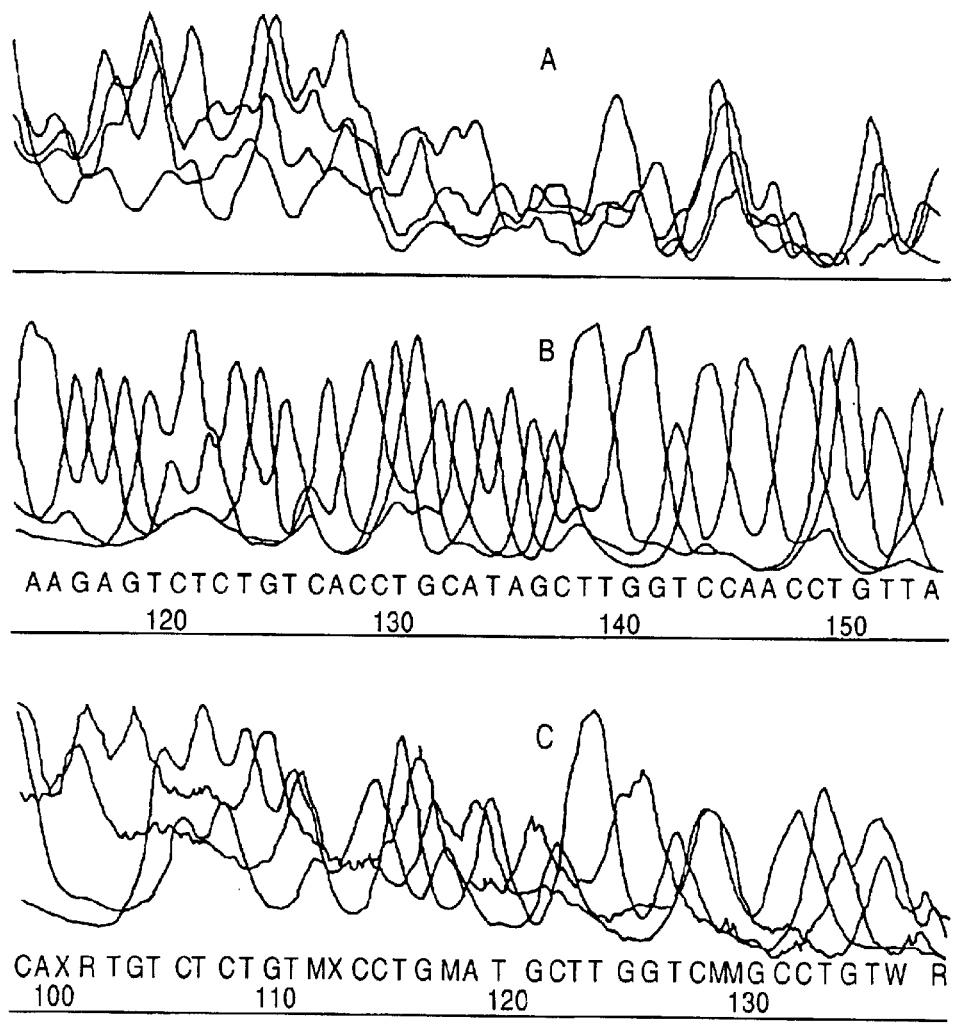
FIG. 3. An uncoupled, direct, exponential amplification and sequencing reaction was carried out in combination with various thermostable polymerases which do not carry the "Tabor-Richardson" mutation. Window A shows a reaction in which 2.5 units Klentaq polymerase were added to a direct, uncoupled amplification and sequencing reaction which was carried out with 60 ng total genomic DNA. Window B shows a direct, uncoupled, exponential amplification and sequencing reaction which was carried out with standard Taq DNA polymerase and window C shows a reaction in which 0.25 units Tth polymerase was added.

Of the thermostable polymerases without a "Tabor-Richardson" mutation, a number of different polymerases were tested with regard to their effect on the direct, exponential amplification and sequencing reaction. Tth polymerase, Klentaq (U.S. Pat. No. 5,436,149, Korolev. S., et al., (1995) *Proc. Natl. Acad. Sci. USA* 92, 9264–9268), Sequitherm and standard Taq DNA polymerase were cycled with 60 ng total genomic DNA. Different unit amounts of 0.25 to 25 units (in the case of Klentaq) were tested for all polymerases (FIG. 3). The best results were achieved with Taq DNA polymerase.

EXAMPLE 5

Figure 4:
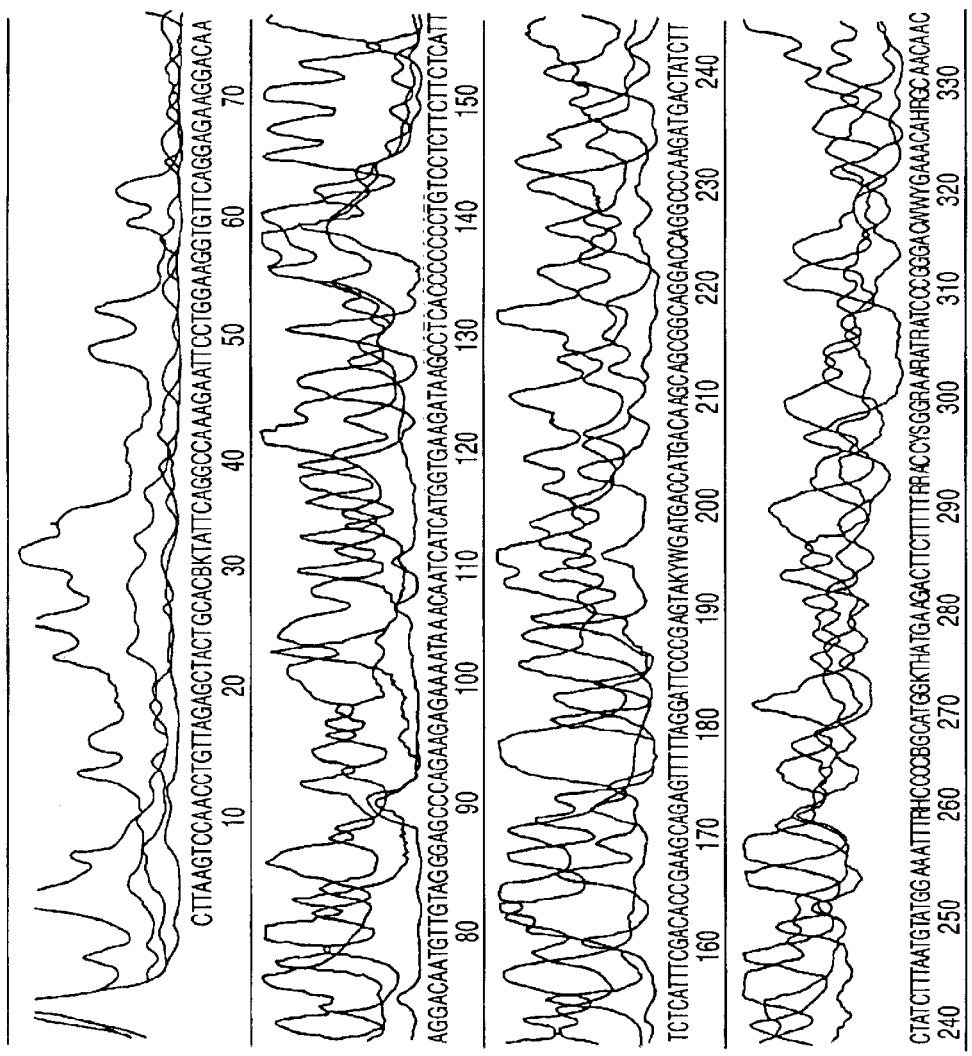
FIG. 4. 300 ng of total genomic human DNA was subjected to a direct, uncoupled, amplification and sequencing reaction using non-equimolar amount of primers i.e. 6 pmol of an FITC-labelled primer (CCR5-2) and 3 pmol of an unlabelled primer (CCR5-3). The primers span a region of 560 base pairs of the human single-copy gene CCR5. The A.L.F. software was able to process 260 bases. The reactions were carried out using 0.25 units Taq DNA polymerase and standard ThermoSequenase reagents.

In order to test whether DEXTAQ can be applied to single-copy DNA sequences if the primers are positioned at a distance of over 500 base pairs to one another, 300 ng total genomic human DNA was subjected to an uncoupled, direct, exponential amplification and sequencing reaction using non-equimolar amounts of an FITC-labelled and of an unlabelled primer (6 pmol:3 pmol) which span a region of 560 base pairs of the human single-copy gene. Good sequence curves were obtained for a length of about 300 base pairs (FIG. 4).

EXAMPLE 6

Figure 5:
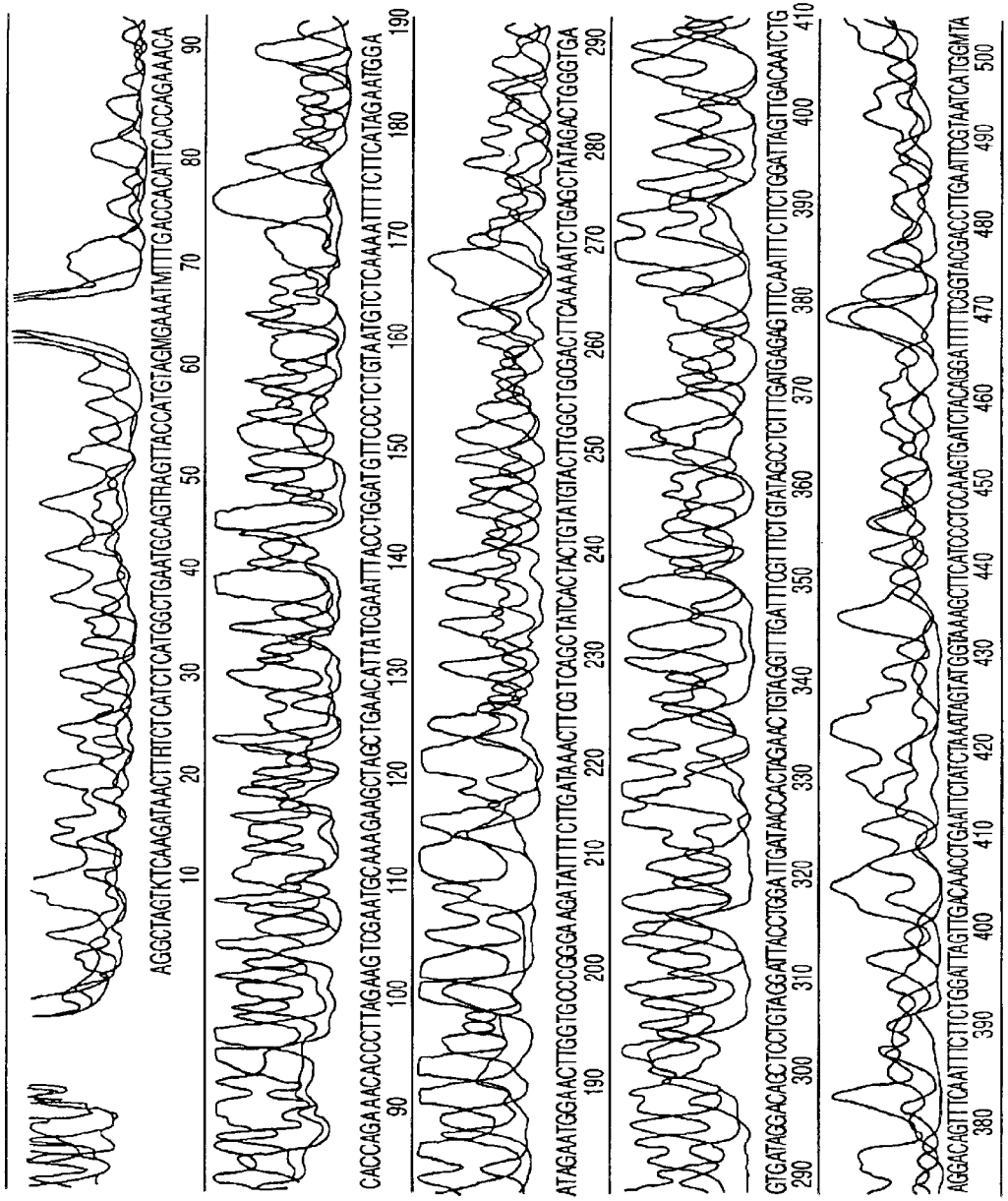
FIG. 5. 4 µl of a bacterial colony lysate was subjected to a direct, uncoupled amplification and sequencing reaction using non-equimolar amounts of differentially labelled primers i.e. 6 pmol of an FITC-labelled primer (universal) and 3 pmol of a Cy5-labelled primer (reverse). The primers span a region of 650 base pairs of the plasmid insert. The A.L.F. software was able to process 502 bases for the FITC labelled primer. The figure shows the curve results in the case of the FITC labelled universal primer. The reactions were carried out using 0.25 units Taq DNA polymerase and standard ThermoSequenase reagents.
Figure 6:
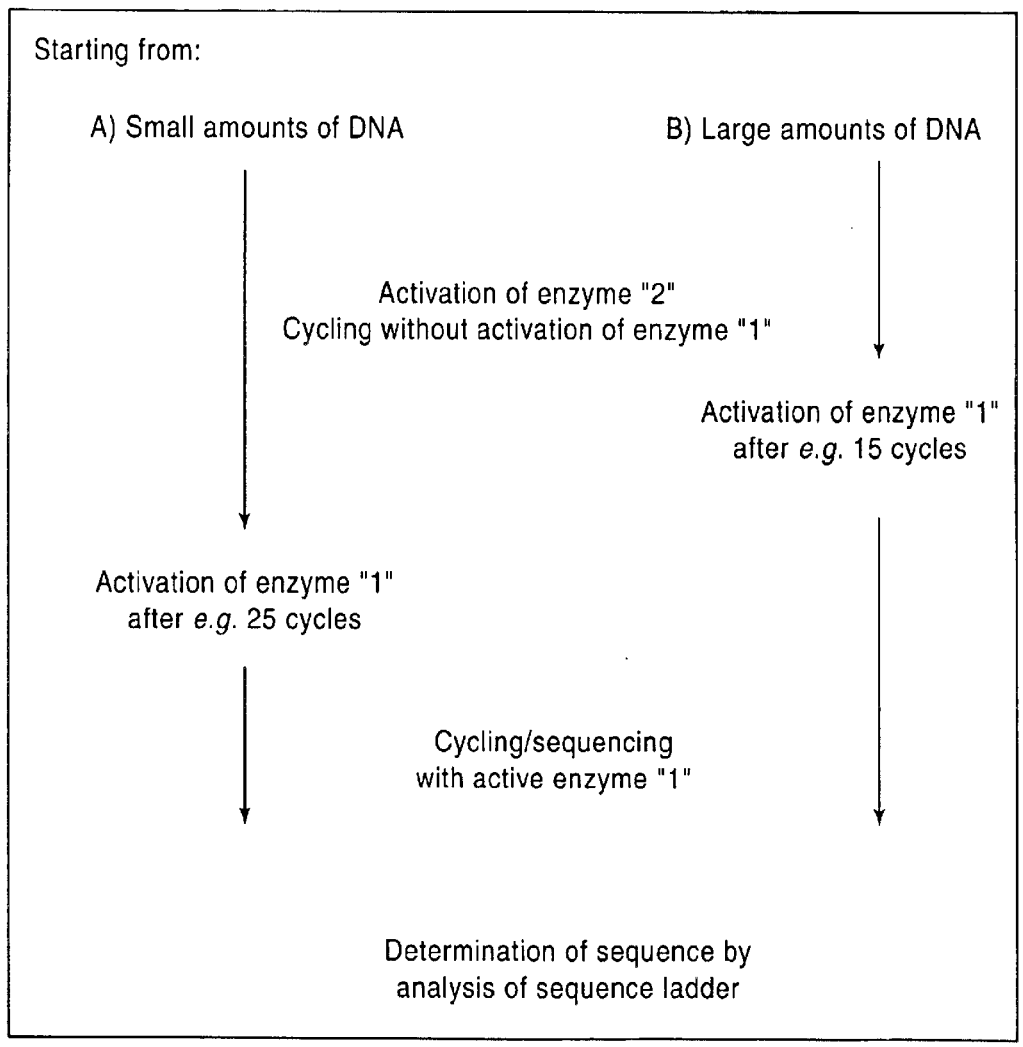
FIG. 6 shows two experiments, (A) one in which a small amount of DNA is used as a substrate and (B) one in which more substrate DNA is present. Initially, the first DNA polymerase is inhibited by a polymerase-inhibiting agent, while the second DNA polymerase is allowed to be active in an amplification phase. By releasing the polymerase-inhibiting agent for the first DNA polymerase only after the amplification phase, this amplification phase can be performed for any given cycle number without the influence of another polymerase.
Figures 7, 7A, 7B:
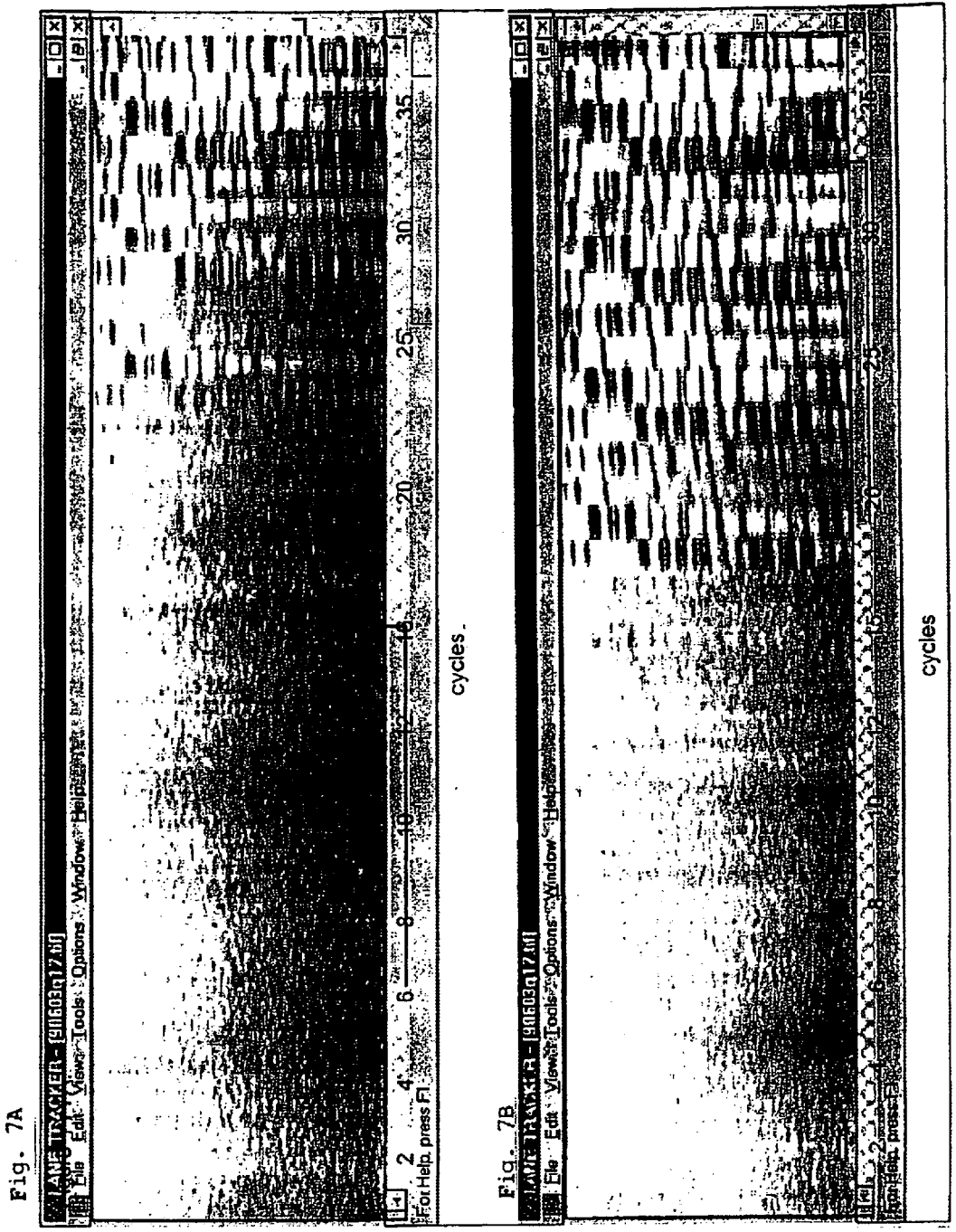
FIG. 7. shows sequential hot-start sequencing ladders produced when 200 ng human genomic DNA was subjected to a uncoupled direct exponential amplification and sequencing reaction.

In order to test whether DEXTAQ can also be applied to plasmid sequencing of crude, bacterial lysates and in order to check whether DEXTAQ can be carried out using two differentially labelled primers, 4 µl of a bacterial colony lysate was subjected to an uncoupled, direct, exponential amplification and sequencing reaction using non-equimolar amounts of differentially labelled primers i.e. 6 pmol of an FITC-labelled primer (universal) and 3 pmol of a Cy5-labelled primer (reverse). The primers span a length of 650 base pairs of the plasmid insert. The A.L.F. software was able in the case of the FITC-labelled primer to process 502 bases (FIG. 5).

TABLE 1a

Non-Complex Mixtures

| A: Size | A: Number of Molecules | A: Total Number of Nucleotides | B: Size | B: Number of Molecules | B: Total Number of Nucleotides |
|---|---|---|---|---|---|
| 1000 bp | $1 \times 10^9$ | $1 \times 10^{12}$ | $3 \times 10^6$ bp | 1000 | $3 \times 10^9$ |

"A" is a target DNA molecule in a PCR product.
"B" represents background DNA molecules in the PCR product.

| Ratio of Number of Molecules (A:B) | Ratio of Total Number of Nucleotides (A:B) |
|---|---|
| $1 \times 10^6$ | 333 |

TABLE 1b

Medium Complex Mixtures

| A: Size | A: Number of Molecules | A: Total Number of Nucleotides | B: Size | B: Number of Molecules | B: Total Number of Nucleotides |
|---|---|---|---|---|---|
| 1000 bp | 300 | $3 \times 10^5$ | $3 \times 10^6$ bp | 1 | $3 \times 10^6$ |

"A" is a target DNA molecule in the DNA from a colony of bacterial cells.
"B" represents background DNA molecules in the DNA from the colony of bacterial cells.

| Ratio of Number of Molecules (A:B) | Ratio of Total Number of Nucleotides (A:B) |
|---|---|
| 300 | 0.1 |

TABLE 1c

| | Complex Mixtures | | | | | Ratio of Number of Molecules (A:B) | Ratio of Total Number of Nucleotides (A:B) |
|---|---|---|---|---|---|---|---|
| A: Size | A: Number of Molecules | A: Total Number of Nucleotides | B: Size | B: Number of Molecules | B: Total Number of Nucleotides | | |
| 1000 bp | 1 | 1000 | $3 \times 10^9$ bp | 1 | $3 \times 10^9$ | 1 | $3 \times 10^{-6}$ |

"A" is an allele or a single copy of a human gene as a target DNA molecule in a human genomic DNA.
"B" represents background DNA molecules in the human genomic DNA.

---

What is claimed is:

1. A method for sequencing at least a portion of a RNA involving converting the RNA to a DNA and simultaneously amplifying the DNA and generating full length and truncated copies of the DNA for sequencing, comprising the steps of
   (a) subjecting a mixture in a single step to a thermocycling reaction, the thermocycling reaction comprises heat denaturation, annealing and synthesis, wherein said mixture comprises
   said RNA,
   a buffer solution,
   a first primer which is able to hybridize with a strand of said DNA,
   a second primer which is able to hybridize with a strand of said DNA
      complementary to the strand with which the first primer is able to hybridize, wherein at least one of the first and second primers is labeled,
   deoxynucleotides or deoxynucleotide derivatives, wherein said deoxynucleotide
      derivatives are able to be incorporated by a thermostable DNA polymerase into growing DNA molecules in place of one of dATP, dGTP, dTTP or dCTP,
   at least one dideoxynucleotide or another terminating nucleotide, and at least two thermostable DNA polymerases,
   wherein said at least two
      thermostable DNA polymerases are at least a first thermostable DNA polymerase and a second thermostable DNA polymerase, which second thermostable DNA polymerase has a reduced ability to incorporate said dideoxynucleotide or another terminating nucleotide compared with said first thermostable DNA polymerase, wherein one of said at least two thermostable DNA polymerases has reverse transcriptase activity,
   to generate full-length and truncated copies of said DNA, wherein the full-length copies have a length equal to that of at least a portion of said DNA spanning the binding sites of the first and second primers;
   (b) separating at least said truncated copies to make a sequence ladder; and thereafter
   (c) reading the sequence ladder to obtain the sequence of said at least a portion of said RNA wherein the conversion of the RNA to the DNA is conducted in the presence of the at least two thermostable DNA polymerases.

2. method of claim 1, wherein the deoxynucleotide derivatives are thionucleotides, 7-deaza-2'-dGTP, 7-deaza-2'-dATP or deoxyinosine triphosphate.

3. The method of claim 1, wherein said another terminating nucleotide is 3'-aminonucleotide or a nucleotide having an ester group at the 3' position.

4. The method of claim 1, wherein said first thermostable DNA polymerase has a reduced discrimination, compared with wild-type Taq DNA polymerase, against said dideoxynucleotide or another terminating nucleotide relative to deoxynucleotides or deoxynucleotide derivatives.

5. The method of claim 4, wherein said first thermostable DNA polymerase is a Taq DNA polymerase lacking 5'-3' exonuclease activity and having a Tabor-Richardson mutation.

6. The method of claim 5, wherein said first thermostable DNA polymerase is AmplitaqFS™, Taquenase™ or Thermo Sequenase™.

7. The method of claim 6, wherein said first thermostable DNA polymerase is Thermo Sequenase™.

8. The method of claim 1, wherein said second thermostable DNA polymerase has reverse transcriptase activity.

9. The method of claim 8, wherein said second thermostable DNA polymerase is Taq DNA polymerase, Tth DNA polymerase, Tfl DNA polymerase, or Klentaq (Taq DNA polymerase) (-exo5'-3'), or a DNA polymerase from Carboxydothermus hydrogenoformans having reverse transcriptase activity.

10. The method of claim 9, wherein said second thermostable DNA polymerase is Taq DNA polymerase, Tth DNA polymerase or Tfl DNA polymerase.

11. The method of claim 1, wherein said first thermostable DNA polymerase is Thermo sequenase™, and said second thermostable DNA polymerase is Taq DNA polymerase.

12. The method of claim 11, wherein said second thermostable DNA polymerase is Tth DNA polymerase, and wherein step (a) is carried out in the presence of MnCl2 or Mn acetate.

13. method of claim 1, wherein the thermocycling reaction in step (a) is carried out without interruption in a single container, vessel or tube.

14. method of claim 1, wherein the ratio of said first primer to said second primer is not equal to 1:1.

15. The method of claim 14, wherein said ratio is between about 2:1 and about 3:1.

16. method of claim 15, wherein said ratio is about 2:1.

17. The method of claim 1, wherein the first and second primers are differently labelled.

18. The method of claim 1, wherein said annealing and synthesis of the thermocycling reaction is carried out at a temperature of at least 55° C.

19. method of claim 1, wherein said RNA in said mixture is a RNA of a single-copy gene.

20. The method of claim 1, wherein said mixture further comprises at least one thermostable pyrophosphatase.

21. The method of claim 1, wherein at least one of the first and second primers has a length that, in combination with a high annealing temperature, prevents annealing to unspecific DNA fragments during the heat denaturation of the thermocycling reaction.

22. The method of claim 21, wherein said length is at least 18 nucleotides.

23. The method of claim 1, wherein said RNA in said mixture is obtained from a body fluid, hairs, a cell, cells or fractions thereof, a tissue or fractions thereof, cell cultures or fractions thereof, bacteria or viruses.

24. The method of claim 1, wherein said RNA in said mixture is unpurified RNA.

25. The method of claim 24, wherein said RNA is total genomic RNA.

26. The method of claim 1, wherein said RNA in said mixture is a RNA of a single-copy gene and said mixture further comprises genomic DNA.

27. The method of claim 1, wherein said annealing and synthesis of the thermocycling reaction is carried out at a temperature of at least about 55° C.

28. The method of claim 27, wherein said annealing and synthesis of the thermocycling reaction is carried out at a temperature of at least about 68° C.

29. The method of claim 1, wherein the molar ratio of said deoxynucleotides or deoxynucleotide derivatives to said at least one dideoxynucleotide or another terminating nucleotide is between about 100:1 and about 1000:1.

30. The method of claim 29, wherein the molar ratio of said deoxynucleotides or deoxynucleotide derivatives to said at least one dideoxynucleotide or another terminating nucleotide is between about 300:1 and about 600:1.

31. The method of claim 1, wherein said deoxynucleotides or deoxynucleotide derivatives are present at a concentration of about 300 mM to about 2 mM.

32. The method of claim 1, wherein said at least one dideoxynucleotide or another terminating nucleotide is present at a concentration of about 1 mM to about 5 mM.

33. The method of claim 1, wherein the length of said DNA is at least 500 nucleotides between the 3' ends of the first and second primers.

34. The method of claim 1, wherein said mixture further comprises at least one polymerase-inhibiting agent against at least one of said at least two thermostable DNA polymerases, wherein said at least one polymerase-inhibiting agent loses inhibitory ability, thereby allowing said at least one of said at least two thermostable DNA polymerases to be active, at a temperature which is at least the temperature at which unspecifically hybridized primers separate from a DNA molecule.

35. The method of claim 34, wherein said at least one polymerase-inhibiting agent inhibits at least said first thermostable DNA polymerase.

36. The method of claim 34, wherein said at least one polymerase-inhibiting agent inhibits at least said second thermostable DNA polymerase.

37. A kit for sequencing at least a portion of a RNA, comprising deoxynucleotides or deoxynucleotide derivatives, which deoxynucleotide derivatives are able to be incorporated by a thermostable DNA polymerase into growing DNA molecules in place of one of dATP, dGTP, dTTP or dCTP;

at least one dideoxynucleotide or another terminating nucleotide; and at least two thermostable DNA polymerases, wherein said at least two thermostable DNA polymerases are at least a first thermostable DNA polymerase and a second thermostable DNA polymerase, which second thermostable DNA polymerase has a reduced ability to incorporate said dideoxynucleotide or another terminating nucleotide in comparison to said first thermostable DNA polymerase, wherein at least one of said at least two thermostable DNA polymerases has reverse transcriptase activity;

wherein the at least two DNA polymers are mixed so that conversion of the RNA to the DNA will be conducted in the presence of the at least two thermostable DNA polymerases.

38. The kit of claim 37, wherein the deoxynucleotide derivatives are thionucleotides, 7-deaza-2'-dGTP, 7-deaza-2'-dATP or deoxyinosine triphosphate.

39. The kit of claim 37, wherein said another terminating nucleotide is 3'-aminonucleotide or a nucleotide having an ester group at the 3' position.

40. The kit of claim 37, wherein said first thermostable DNA polymerase has a reduced discrimination, compared with wild-type Taq DNA polymerase, against said dideoxynucleotide or another terminating nucleotide relative to deoxynucleotides or deoxynucleotide derivatives.

41. The kit of claim 40, wherein said first thermostable DNA polymerase is a Taq DNA polymerase lacking 5'-3' exonuclease activity and having a Tabor-Richardson mutation.

42. The kit of claim 41, wherein said first thermostable DNA polymerase is AmplitaqFS™, Taquenase™, or ThermoSequenase™.

43. The kit of claim 42, wherein said first thermostable DNA polymerase is ThemoSequenase™.

44. The kit of claim 37, wherein said second thermostable DNA polymerase is Taq DNA polymerase, Tth DNA polymerase, Tfl DNA polymerase, or Klentaq (Taq DNA polymerase) (-exo5'-3'), or a DNA polymerase from Carboxydothermus hydrogenoformans having reverse transcriptase activity.

45. The kit of claim 44, wherein said second thermostable DNA polymerase is Taq DNA polymerase.

46. The kit of claim 37, further comprising MnCl.sub.2 or Mn acetate, wherein said second thermostable DNA polymerase is Tth DNA polymerase.

47. The kit of claim 37, wherein the ratio of said first primer to said second primer is not equal to 1:1.

48. The kit of claim 47, wherein said ratio is between about 2:1 and about 3:1.

49. The kit of claim 48, wherein said ratio is 2:1.

50. The kit of claim 37, further comprising at least one thermostable pyrophosphatase.

51. The kit of claim 37, further comprises at least one polymerase-inhibiting agent against at least one of said at least two thermostable DNA polymerases, wherein said at least one polymerase-inhibiting agent loses inhibitory ability, thereby allowing said at least one of said at least two thermostable DNA polymerases to be active, at a temperature which is at least the temperature at which unspecifically hybridized primers separate from a DNA molecule.

52. The kit of claim 51, wherein said at least one polymerase-inhibiting agent inhibits at least said first thermostable DNA polymerase.

53. The kit of claim 51, wherein said at least one polymerase-inhibiting agent inhibits at least said second thermostable DNA polymerase.

54. The kit of claim 51, wherein said agent is an acid anhydnde.

55. The kit of claim 54, wherein said agent is citraconic anhydride, cis-aconitic anhydride, phthalic anhydride, succinic anhydride or maleic anhydride.

56. The kit of claim 51, wherein said agent is a compound having at least one acid anhydride group per molecule.

57. The kit of daim 56, wherein said agent is a compound having two acid anhydride groups per molecule.

58. The kit of claim 57, wherein said agent is pyromellitic dianhydride or naphthalenetetracarboxylic dianhydride.

59. The method of claim 34, wherein said agent is an acid anhydride.

60. The method of claim 59, wherein said agent is citraconic anhydride, cis-aconitic anhydride, phthalic anhydnde, succinic anhydride or maleic anhydride.

61. The method of claim 34, wherein said agent is a compound having at least one acid anhydride group per molecule.

62. The method of claim 61, wherein said agent is a compound having two acid anhydride groups per molecule.

63. The method of claim 62, wherein said agent is pyromellitic dianhydride or naphthalenetetracarboxylic dianhydride.

64. A method for sequencing at least a portion of a DNA involving simultaneously amplifying the DNA and generating full length and truncated copies of the DNA for sequencing, comprising the steps of (a) subjecting a mixture in a single step to a thermocycling reaction, the thermocycling reaction comprises heat denaturation, annealing and synthesis, wherein said mixture comprises said DNA, a buffer solution, a first primer which is able to hybridize with a strand of said DNA, a second primer which is able to hybridize with a strand of said DNA complementary to the strand with which the first primer is able to hybridize, wherein at least one of the first and second primers is labelled, deoxynucleotides or deoxynucleotide derivatives, wherein said deoxynucleotide derivatives are able to be incorporated by a thermostable DNA polymerase into growing DNA molecules in place of one of dATP, dGTP, dTTP or dCTP, at least one dideoxynucleotide or another terminating nucleotide, at least two thermostable DNA polymerases, wherein said at least two thermostable DNA polymerases are at least a first thermostable DNA polymerase and a second thermostable DNA polymerase, which second thermostable DNA polymerase has a reduced ability to incorporate said dideoxynucleotide or another terminating nucleotide compared with said first thermostable DNA polymerase, and at least one polymerase-inhibiting agent against at least one of said at least two thermostable DNA polymerases, wherein said at least one polymerase-inhibiting agent loses inhibitory ability, thereby allowing said at least one of said at least two thermostable DNA polymerases to be active, at a temperature which is at least the temperature at which unspecifically hybridized primers separate from a DNA molecule, to generate full-length and truncated copies of said DNA, wherein the full-length copies have a length equal to that of at least a portion of said DNA spanning the binding sites of the first and second primers; (b) separating at least said truncated copies to make a sequence ladder; and thereafter (c) reading the sequence ladder to obtain the sequence of said at least a portion of said DNA.

65. The method of claim 64, wherein the deoxynucleotide derivatives are thionucleotides, 7-deaza-2'-dGTP, 7-deaza-2'-dATP or deoxyinosine triphosphate.

66. The method of claim 64, wherein said another terminating nucleotide is 3'-aminonucleotide or a nucleotide having an ester group at the 3' position.

67. The method of claim 64, wherein said first thermostable DNA polymerase has a reduced discrimination, compared with wild-type Taq DNA polymerase, against said dideoxynucleotide or another terminating nucleotide relative to deoxynucleotides or deoxynucleotide derivatives.

68. The method of claim 67, wherein said first thermostable DNA polymerase is a Taq DNA potymerase lacking 5'-3' exonuclease activity and having a Tabor-Richardson mutation.

69. The method of claim 68, wherein said first thermostable DNA polymerase is AmplitaqFS™, Taquenase™, Thermo Sequenase™.

70. The method of claim 69, wherein said first thermostable DNA polymerase is Thermo Sequenase™.

71. The method of claim 64, wherein said at least one polymerase inhibiting agent has at least one said anhydride group per molecule.

72. The method of claim 64, wherein said second thermostable DNA polymerase is Taq DNA polymerase, Tth DNA polymerase, Tfl DNA polymerase, or Klentaq (Taq DNA polymerase) (-exo5'-3').

73. The method of claim 72, wherein said second thermostable DNA polymerase is Taq DNA polymerase, Tth DNA polymerase or Tfl DNA polymerase.

74. The method of claim 64, wherein said first thermostable DNA polymerase is Thermo Sequenase™, and said second thermostable DNA polymerase is Taq DNA polymerase.

75. The method of claim 74, wherein said second thermostable DNA polymerase is Tth DNA polymerase and wherein step (a) is carried out in the presence of MnCl.MnCl$_2$ or Mn acetate.

76. The method of claim 64, wherein the thermocycling reaction in step (a) is carried out without interruption in a single container, vessel or tube.

77. The method of claim 64, wherein the ratio of said first primer to said second primer is not equal to 1:1.

78. The method of claim 77, wherein said ratio is between about 2:1 and about 3:1.

79. The method of claim 78, wherein said ratio is about 2:1.

80. The method of claim 64, wherein the first and second primers are differently labelled.

81. The method of claim 64, wherein said annealing and synthesis of the thermocycling reaction is carried out at a temperature of at least 55° C.

82. The method of claim 64, wherein said DNA in said mixture is a single-copy DNA in a complex mixture of DNA.

83. The method of claim 64, wherein said mixture further comprises at least one thermostable pyrophosphatase.

84. The method of claim 64, wherein at least one of the first and second primers has a length that, in combination with a high annealing temperature, prevents annealing to unspecific DNA fragments during the heat denaturation of the thermocycling reaction.

85. The method of claim 84, wherein said length is at least 18 nucleotides.

86. The method of claim 64, wherein said DNA in said mixture is obtained from a body fluid, hairs, a cell, cells or fractions thereof, a tissue or fractions thereof, cell cultures or fractions thereof, bacteria or viruses.

87. The method of claim 64, wherein said DNA in said mixture is unpurified DNA.

88. The method of claim 87, wherein said DNA is total genomic DNA.

89. The method of claim 64, wherein said DNA in said mixture is a single-copy DNA, wherein said mixture further comprises total genomic DNA.

90. method of claim 64, wherein said annealing and synthesis of the thermocycling reaction is carried out at a temperature of at least about 55° C.

91. method of claim 90, wherein said annealing and synthesis of the thermocycling reaction is carried out at a temperature of at least about 68° C.

92. method of claim 64, wherein the molar ratio of said deoxynucleotides or deoxynucleotide derivatives to said at least one dideoxynucleotide or another terminating nucleotide is between about 100:1 and about 1000:1.

93. method of claim 92, wherein the molar ratio of said deoxynucleotides or deoxynucleotide derivatives to said at least one dideoxynucleotide or another terminating nucleotide is between about 300:1 and about 600:1.

94. The method of claim 64, wherein said deoxynucleotides or deoxynucleotide derivatives are present at a concentration of about 300 mM to 2 mM.

95. The method of claim 64, wherein said at least one dideoxynucleotide or another terminating nucleotide is present at a concentration of about 1 to 5 mM.

96. The method of claim 64, wherein the length of the DNA in said mixture is at least 500 nucleotides between the 3' ends of the first and second primers.

97. The method of claim 64, wherein said at least one polymerase-inhibiting agent inhibits at least said first thermostable DNA polymerase.

98. The method of claim 64, wherein said at least one polymerase-inhibiting agent inhibits at least said second thermostable DNA polymerase.

99. The method of claim 64, wherein said at least one polyrnerase-inhibiting agent reversibly loses inhibitory activity at the temperature which is at least the temperature at which unspecifically hybridized primers separate from a DNA molecule, thereby enabling said agent to inhibit said at least one of said at least two thermostable DNA polymerases in more than one thermocycle.

100. A kit for sequencing at least a portion of a DNA, comprising deoxynucleotides or deoxynucleotide derivatives, which deoxynucleotide derivatives are able to be incorporated by a thermostable DNA polymerase into growing DNA molecules in place of one of dATP, dGTP, dTTP or dCTP; at least one dideoxynucteotide or another terminating nucleotide; at least two thermostable DNA polymerases, wherein said at least two thermostable DNA polymerases are at least a first thermostable DNA polymerase and a second thermostable DNA polymerase, which second thermostable DNA polymerase has a reduced ability to incorporate said dideoxynucteotide or another terminating nucleotide in comparison to said first thermostable DNA polymerase; and at least one polymerase-inhibiting agent against at least one of said at least two thermostable DNA polymerases, wherein said at least one polymerase-inhibiting agent loses inhibitory ability, thereby allowing said at least one of said at least two thermostable DNA polymerases to be active, at a temperature which is at least the temperature at which unspecifically hybridized primers separate from a DNA molecule, wherein said at least one polymerase-inhibting agent is a compound having at least one acid anhydride group per molecule.

101. The kit of claim 100, wherein the deoxynucleotide derivatives are thionucleotides, 7-deaza-2'-dGTP, 7-deaza-2'-dATP or deoxyinosine triphosphate.

102. The kit of claim 100, wherein said another terminating nucleotide is 3'-amlnonucleotide or a nucleotide having an ester group at the 3' position.

103. The kit of claim 100, wherein said first thermostable DNA polymerase has a reduced discrimination, compared with wild-type Taq DNA polymerase, against said dideoxynucleotide or another terminating nucleotide relative to deoxynucleotides or deoxynucleotide derivatives.

104. The kit of claim 103, wherein said first thermostable DNA polymerase is a Taq DNA polymerase lacking 5'-3' exonuclease activity and having a Tabor-Richardson mutation.

105. The kit of claim 104, wherein said first thermostable DNA polymerase is AmplitaqFS™, Taquenasetm™, or ThermoSequenase™.

106. The kit of claim 105, wherein said first thermostable DNA polymerase is ThermoSequenase™.

107. The kit of claim 100, wherein said second thermostable DNA polymerase is Taq DNA polymerase, Tth DNA polymerase, Tfl DNA polymerase, or Klentaq (Taq DNA polymerase) (-exo5'-3'), or a DNA polymerase from Carboxydothermus hydrogenoformans having reverse transcriptase activity.

108. The kit of claim 107, wherein said second thermostable DNA polymerase is Taq DNA polymerase.

109. The kit of claim 100, further comprising MnCl.sub.2 or Mn acetate, wherein said second thermostable DNA polymerase is Tth DNA polymerase.

110. The kit of claim 100, wherein the ratio of said first primer to said second primer is not equal to 1:1.

111. The kit of claim 110, wherein said ratio is between about 2:1 and about 3:1.

112. The kit of claim 111, wherein said ratio is about 2:1.

113. The kit of claim 100, further comprising at least one thermostable pyrophosphatase.

114. The kit of claim 100, wherein said at least one polymerase-inhibiting agent inhibits at least said first thermostable DNA polymerase.

115. The kit of claim 100, wherein said at least one polymerase-inhibiting agent inhibits at least said second thermostable DNA polymerase.

116. The kit of claim 100, further comprises an antibody against one of said at least two thermostable DNA polymerases, wherein said antibody loses inhibitory ability, thereby allowing said one of said at least two thermostable DNA polymerases to be active, at a temperature which is at least the temperature at which unspecifically hybridized primers separate from a DNA molecule.

117. The kit of claim 116, wherein inhibition of said one of said at least two thermostable DNA polymerases by said antibody begins at a lower temperature than inhibition of said at least one of said at least two thermostable DNA polymerases by said polymerase-inhibiting agent.

118. The kit of claim 100, wherein said polymerase-inhibiting agent is citraconic anhydride, cis-aconitic anhydride, phthalic anhydride, succinic anhydride or maleic anhydride.

119. The kit of claim 100, wherein said polymerase-inhibiting agent is a compound having two acid anhydride groups per molecule.

120. The kit of claim 119, wherein said agent is pyromellitic dianhydride or naphthalenetetracarboxylic dianhydride.

121. The kit of claim 100, wherein said at least one polymerase-inhibiting agent reversibly loses inhibitory activity at the temperature which is at least the temperature at which unspecifically hybridized primers separate from a DNA molecule, thereby enabling said agent to inhibit said at least one of said at least two thermostable DNA polymerases in more than one thermocycle.

122. The method of claim 64, wherein said mixture further comprises an antibody against one of said at least two thermostable DNA polymerases, wherein said antibody loses inhibitory ability, thereby allowing said one of said at least two thermostable DNA polymerases to be active, at a temperature which is at least the temperature at which unspecifically hybridized primers separate from a DNA molecule.

123. The method of claim 122, wherein inhibition of said one of said at least two thermostable DNA polymerases by said antibody begins at a lower temperature than inhibition of said at least one of said at least two thermostable DNA polymerases by said polymerase-inhibiting agent.

124. The method of claim 71, wherein said polymerase-inhibiting agent is citraconic anhydride, cis-aconitic anhydride, phthalic anhydride, succinic anhydride or maleic anhydride.

125. The method of claim 71, wherein said agent is a compound having two acid anhydride groups per molecule.

126. The method of claim 125, wherein said agent is pyromellitic dianhyd ride or naphthalenetetracarboxylic dianhydride.

127. The method of claim 64, wherein said mixture further comprises at least one agent that lowers the melting point of the DNA.

128. The method of claim 127, wherein said at least one agent is selected from the group consisting of glycerin, trehalose, betaine and DMSO.

129. The method of claim 97, wherein an inhibitory activity of said at least one polymerase-inhibiting agent is reversibly reduced at a specific temperature and after a specific number of thermocycles allowing sequencing of the DNA to start after the DNA has been amplified.

130. The method of claim 129, wherein the inhibitory activity of said at least one polymerase-inhibiting agent is reversibly reduced when the reaction mixture is exposed at an elevated temperature.

131. The method of claim 130, wherein said first thermostable DNA polymerase is a DNA polymerase which carries a Tabor-Richardson mutation and has no 5' to 3' exonuclease activity.

132. The method of claim 131, wherein said first thermostable DNA polymerase is selected from the group consisting of AMPLITAQ FS™, TAQUENASE™, and THERMOSEQUENASE.

133. The kit of claim 100 further comprising at least one agent that lowers the melting point of the DNA.

134. The kit of claim 133, wherein said at least one agent is selected from the group consisting of glycerin, trehalose, betaine and DMSO.

135. The method of claim 8, wherein said mixture further comprises a polymerase-inhibiting agent against said second thermostable DNA polymerase.

136. The method of claim 135, wherein an inhibitory activity of said polymerase-inhibiting agent is reduced after reversed transcription of the RNA.

137. The kit of claim 124 wherein said polymerase-inhibiting agent is citraconic anhydride.

138. The method of claim 64 further comprising, prior to step (a), a step of mixing all of said DNA, said buffer solution, said first primer, said second primer, said deoxynucleotides or deoxynucleotide derivatives, said dideoxynucleotide or other terminating nucleotide, the at least two thermostable DNA polymerases and the at least one polymerase-inhibiting agent in a single container, vessel or tube.

* * * * *